US010782294B2

(12) United States Patent
Henn et al.

(10) Patent No.: US 10,782,294 B2
(45) Date of Patent: *Sep. 22, 2020

(54) PEPTIDES DERIVED FROM MYOSIN 19 AND METHODS OF USE THEREOF

(71) Applicant: TECHNION RESEARCH & DEVELOPMENT FOUNDATION LIMITED, Haifa (IL)

(72) Inventors: Arnon Henn, Misgav (IL); Boris Shneyer, Afula (IL); Andreas Reichert, Düsseldorf (DE)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,049

(22) Filed: Jul. 23, 2018

(65) Prior Publication Data

US 2018/0328926 A1    Nov. 15, 2018

Related U.S. Application Data

(63) Continuation of application No. 14/963,635, filed on Dec. 9, 2015, now Pat. No. 10,036,749.

(30) Foreign Application Priority Data

Dec. 9, 2014 (GB) .................................. 1421888.7

(51) Int. Cl.
| C07K 14/00 | (2006.01) |
| C07K 14/47 | (2006.01) |
| C07K 7/06 | (2006.01) |
| C07K 7/08 | (2006.01) |
| G01N 33/569 | (2006.01) |

(52) U.S. Cl.
CPC ... *G01N 33/56966* (2013.01); *C07K 14/4716* (2013.01); *G01N 2333/4712* (2013.01)

(58) Field of Classification Search
CPC . C07K 14/00; C07K 7/06; C07K 7/08; C07K 14/4716; C07K 14/47; G01N 2333/4712; G01N 33/56966
USPC ....... 530/300, 324, 325, 326, 327, 328, 329, 530/330; 435/29, 7.1
See application file for complete search history.

(56) References Cited

U.S. PATENT DOCUMENTS

| 7,745,391 B2 * | 6/2010 | Mintz ..................... A61P 35/00 514/19.3 |
| 7,833,706 B2 | 11/2010 | Begovich et al. |
| 2003/0040471 A1 | 2/2003 | Watson et al. |

OTHER PUBLICATIONS

Omar A. Quintero el at: "Humna Myo19 Is a Novel Myosin that Associates with Mitochondria", Current Biology, vol. 19, Dec. 15, 2009, pp. 2008-2013 (6 pages).
Doron Rapaport: "Finding the Right Organelle; Targeting Signals in Mitochondrial Outer Membrane Proteins", EMBO Reports, vol. 4, No. 10, May 27, 2003, pp. 948-952 (5 pages).
M. Amanda Hartman et al: "The myosin superfamily at a glance", Cell Science at a Glance, Journal of Cell Science, vol. 125, 2012, pp. 1627-1632 (6 pages).
Sarah Woolner et al: "Unconventional myosins acting unconventionally", Trends Cell Biol. vol. 19, No. 6, Jun. 2009, pp. 245-252 (17 pages).
UniProt B7Z1T7, pp. 104, Integrated into UniProt/TrEMBL on Mar. 3, 2009.

* cited by examiner

*Primary Examiner* — Julie Ha
(74) *Attorney, Agent, or Firm* — Roach, Brown, McCarthy & Gruber, P.C.; Kevin D. McCarthy

(57) ABSTRACT

Isolated peptides and compositions comprising same are provided. Further, methods for targeting mitochondria in a cell, methods for assessing mitochondrial function in a cell and methods for diagnosing mitochondria associated diseases are provided.

9 Claims, 31 Drawing Sheets
(28 of 31 Drawing Sheet(s) Filed in Color)
Specification includes a Sequence Listing.

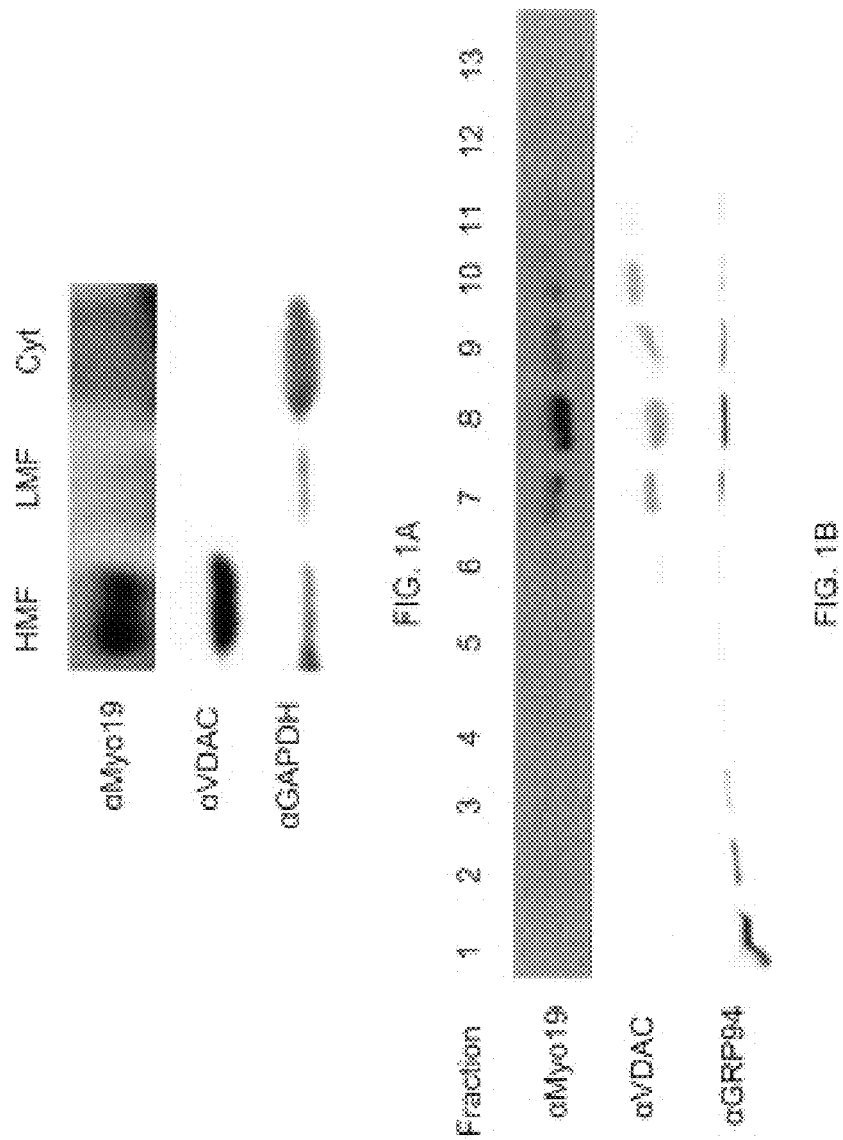

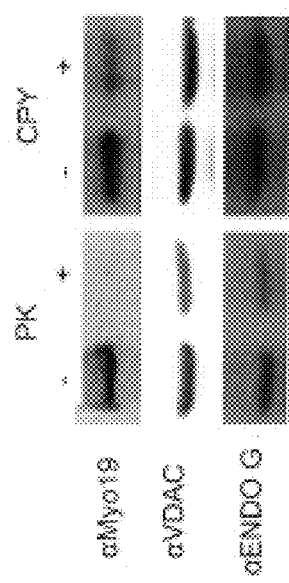
FIG. 1C
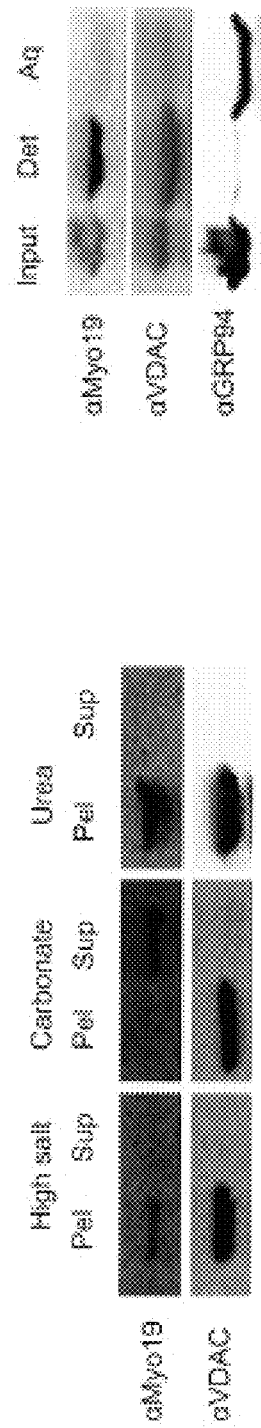
FIG. 1E
FIG. 1D

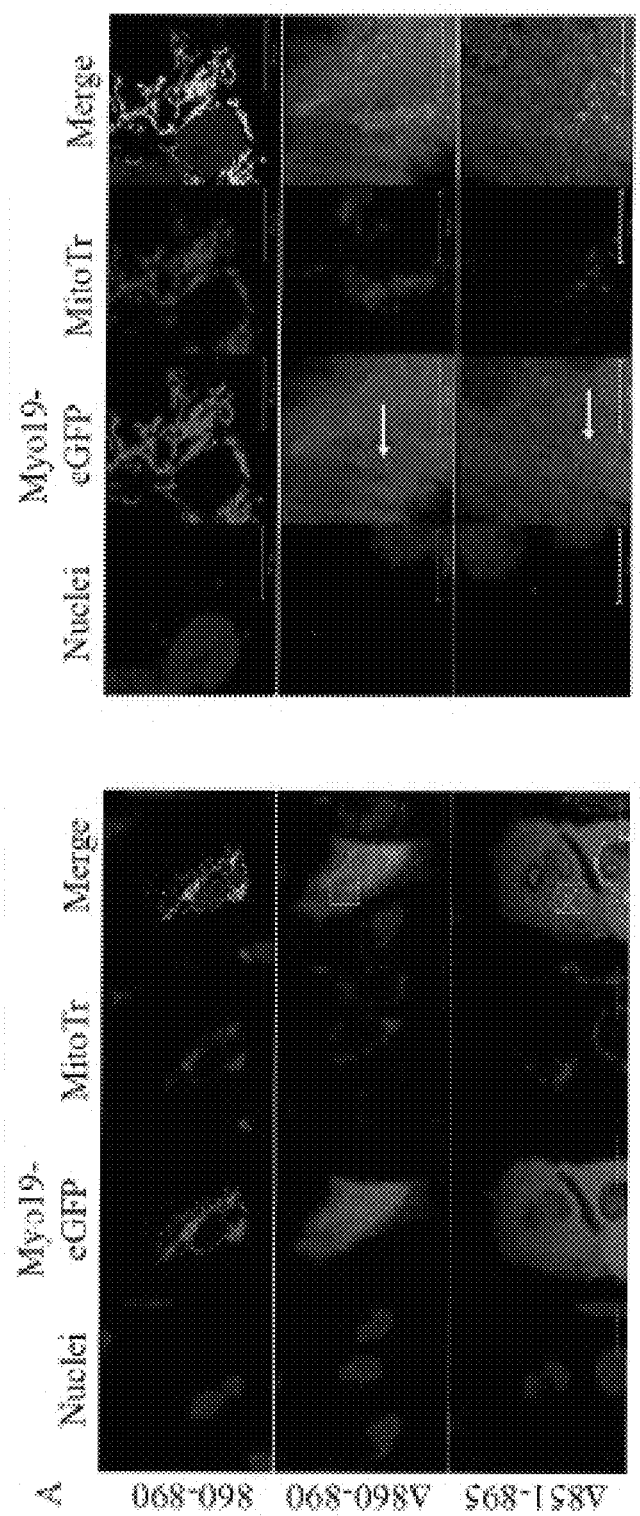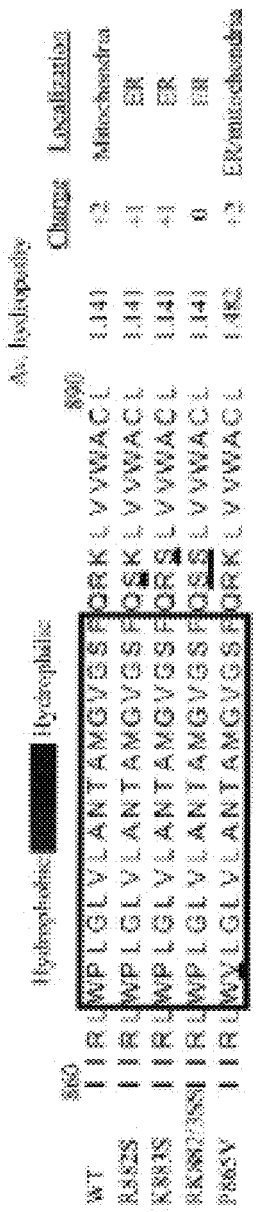
FIG. 2A
FIG. 2B

```
                         SEQUENCE LISTING

<160> NUMBER OF SEQ ID NOS: 33

<210> SEQ ID NO 1
   <211> LENGTH: 17
   <212> TYPE: PRT
   <213> ORGANISM: artificial sequence
   <220> FEATURE:
   <223> OTHER INFORMATION: synthetic
   <220> FEATURE:
   <221> NAME/KEY: MISC_FEATURE
   <222> LOCATION: (2)..(2)
   <223> OTHER INFORMATION: X is Proline or Valine

<400> SEQUENCE: 1

Trp Xaa Leu Gly Leu Val Leu Ala Asn Thr Ala Met Gly Val Gly Ser
   1               5                   10                  15

Phe

<210> SEQ ID NO 2
   <211> LENGTH: 17
   <212> TYPE: PRT
   <213> ORGANISM: artificial sequence
   <220> FEATURE:
   <223> OTHER INFORMATION: synthetic

<400> SEQUENCE: 2

Trp Pro Leu Gly Leu Val Leu Ala Asn Thr Ala Met Gly Val Gly Ser
   1               5                   10                  15

Phe

<210> SEQ ID NO 3
   <211> LENGTH: 31
   <212> TYPE: PRT
   <213> ORGANISM: artificial sequence
   <220> FEATURE:
   <223> OTHER INFORMATION: synthetic

<400> SEQUENCE: 3

Ile Ile Arg Leu Trp Pro Leu Gly Leu Val Leu Ala Asn Thr Ala Met
   1               5                   10                  15

Gly Val Gly Ser Phe Gln Arg Lys Leu Val Val Trp Ala Cys Leu
                   20                  25                  30

<210> SEQ ID NO 4
   <211> LENGTH: 37
   <212> TYPE: PRT
   <213> ORGANISM: artificial sequence
   <220> FEATURE:
```

<223> OTHER INFORMATION: synthetic

<400> SEQUENCE: 4

Leu Leu Glu Ala Ile Ile Arg Leu Trp Pro Leu Gly Leu Val Leu Ala
1               5                   10                  15

Asn Thr Ala Met Gly Val Gly Ser Phe Gln Arg Lys Leu Val Val Trp
            20                  25                  30

Ala Cys Leu Gln Leu
        35

<210> SEQ ID NO 5
<211> LENGTH: 17
<212> TYPE: PRT
<213> ORGANISM: artificial sequence
<220> FEATURE:
<223> OTHER INFORMATION: synthetic

<400> SEQUENCE: 5

Trp Val Leu Gly Leu Val Leu Ala Asn Thr Ala Met Gly Val Gly Ser
1               5                   10                  15

Phe

<210> SEQ ID NO 6
<211> LENGTH: 31
<212> TYPE: PRT
<213> ORGANISM: artificial sequence
<220> FEATURE:
<223> OTHER INFORMATION: synthetic

<400> SEQUENCE: 6

Ile Ile Arg Leu Trp Val Leu Gly Leu Val Leu Ala Asn Thr Ala Met
1               5                   10                  15

Gly Val Gly Ser Phe Gln Arg Lys Leu Val Val Trp Ala Cys Leu
            20                  25                  30

<210> SEQ ID NO 7
<211> LENGTH: 37
<212> TYPE: PRT
<213> ORGANISM: artificial sequence
<220> FEATURE:
<223> OTHER INFORMATION: synthtetic

<400> SEQUENCE: 7

Leu Leu Glu Ala Ile Ile Arg Leu Trp Val Leu Gly Leu Val Leu Ala
1               5                   10                  15

Asn Thr Ala Met Gly Val Gly Ser Phe Gln Arg Lys Leu Val Val Trp
            20                  25                  30

Ala Cys Leu Gln Leu
        35

<210> SEQ ID NO 8
<211> LENGTH: 31
<212> TYPE: PRT
<213> ORGANISM: artificial sequence
<220> FEATURE:
<223> OTHER INFORMATION: synthetic

<400> SEQUENCE: 8

Ile Ile Arg Leu Trp Pro Leu Gly Leu Val Leu Ala Asn Thr Ala Met
1               5                   10                  15

Gly Val Gly Ser Phe Gln Ser Lys Leu Val Val Trp Ala Cys Leu
            20                  25                  30

-continued

```
<210> SEQ ID NO 9
<211> LENGTH: 31
<212> TYPE: PRT
<213> ORGANISM: artificial sequence
<220> FEATURE:
<223> OTHER INFORMATION: synthetic

<400> SEQUENCE: 9

Ile Ile Arg Leu Trp Pro Leu Gly Leu Val Leu Ala Asn Thr Ala Met
1               5                   10                  15

Gly Val Gly Ser Phe Gln Arg Ser Leu Val Val Trp Ala Cys Leu
            20                  25                  30

<210> SEQ ID NO 10
<211> LENGTH: 31
<212> TYPE: PRT
<213> ORGANISM: artificial sequence
<220> FEATURE:
<223> OTHER INFORMATION: synthetic

<400> SEQUENCE: 10

Ile Ile Arg Leu Trp Pro Leu Gly Leu Val Leu Ala Asn Thr Ala Met
1               5                   10                  15

Gly Val Gly Ser Phe Gln Ser Ser Leu Val Val Trp Ala Cys Leu
            20                  25                  30

<210> SEQ ID NO 11
<211> LENGTH: 31
<212> TYPE: PRT
<213> ORGANISM: artificial sequence
<220> FEATURE:
<223> OTHER INFORMATION: synthetic

<400> SEQUENCE: 11

Ile Ile Arg Leu Trp Val Leu Gly Leu Val Leu Ala Asn Thr Ala Met
1               5                   10                  15

Gly Val Gly Ser Phe Gln Arg Lys Leu Val Val Trp Ala Cys Leu
            20                  25                  30

<210> SEQ ID NO 12
<211> LENGTH: 45
<212> TYPE: PRT
<213> ORGANISM: artificial sequence
<220> FEATURE:
<223> OTHER INFORMATION: synthetic

<400> SEQUENCE: 12

Pro Leu Gln Thr Arg Leu Leu Glu Ala Ile Ile Arg Leu Trp Pro Leu
1               5                   10                  15

Gly Leu Val Leu Ala Asn Thr Ala Met Gly Val Gly Ser Phe Gln Arg
            20                  25                  30

Lys Leu Val Val Trp Ala Cys Leu Gln Leu Pro Arg Gly
        35                  40                  45

<210> SEQ ID NO 13
<211> LENGTH: 26
<212> TYPE: PRT
<213> ORGANISM: artificial sequence
<220> FEATURE:
<223> OTHER INFORMATION: synthetic

<400> SEQUENCE: 13

Glu Ala Ile Ile Arg Leu Trp Pro Leu Gly Leu Val Leu Ala Asn Thr
1               5                   10                  15
```

Ala Met Gly Val Gly Ser Phe Gln Arg Lys
         20                  25

<210> SEQ ID NO 14
<211> LENGTH: 26
<212> TYPE: PRT
<213> ORGANISM: artificial sequence
<220> FEATURE:
<223> OTHER INFORMATION: synthetic

<400> SEQUENCE: 14

Glu Ala Ile Ile Arg Leu Trp Pro Leu Gly Leu Val Leu Ala Asn Thr
1               5                   10                  15

Ala Met Gly Val Gly Ser Phe Gln Ser Ser
         20                  25

<210> SEQ ID NO 15
<211> LENGTH: 32
<212> TYPE: PRT
<213> ORGANISM: artificial sequence
<220> FEATURE:
<223> OTHER INFORMATION: synthetic

<400> SEQUENCE: 15

Phe Arg Trp Gly Lys Pro Val Gly Lys Lys Arg Arg Pro Val Lys Val
1               5                   10                  15

Tyr Pro Asn Gly Ala Glu Asp Glu Ser Ala Glu Ala Phe Pro Leu Glu
            20                  25                  30

<210> SEQ ID NO 16
<211> LENGTH: 20
<212> TYPE: DNA
<213> ORGANISM: artificial sequence
<220> FEATURE:
<223> OTHER INFORMATION: synthetic

<400> SEQUENCE: 16
catggcgatc gctagcggat                                           20

<210> SEQ ID NO 17
<211> LENGTH: 21
<212> TYPE: DNA
<213> ORGANISM: artificial sequence
<220> FEATURE:
<223> OTHER INFORMATION: synthetic

<400> SEQUENCE: 17
ataatccgcc tctggcccct g                                         21

<210> SEQ ID NO 18
<211> LENGTH: 20
<212> TYPE: DNA
<213> ORGANISM: artificial sequence
<220> FEATURE:
<223> OTHER INFORMATION: synthetic

<400> SEQUENCE: 18
gaggcaagcc cagaccacta                                           20

<210> SEQ ID NO 19
<211> LENGTH: 21
<212> TYPE: DNA
<213> ORGANISM: artificial sequence
<220> FEATURE:
<223> OTHER INFORMATION: synthetic

```
<400> SEQUENCE: 19
ggcgaacaaa agcttcgaat t                                            21

<210> SEQ ID NO 20
<211> LENGTH: 20
<212> TYPE: DNA
<213> ORGANISM: artificial sequence
<220> FEATURE:
<223> OTHER INFORMATION: synthetic

<400> SEQUENCE: 20
gaggcaagcc cagaccacta                                              20

<210> SEQ ID NO 21
<211> LENGTH: 21
<212> TYPE: DNA
<213> ORGANISM: artificial sequence
<220> FEATURE:
<223> OTHER INFORMATION: synthetic

<400> SEQUENCE: 21
ggcgaacaaa agcttcgaat t                                            21

<210> SEQ ID NO 22
<211> LENGTH: 24
<212> TYPE: DNA
<213> ORGANISM: artificial sequence
<220> FEATURE:
<223> OTHER INFORMATION: synthetic

<400> SEQUENCE: 22
ctgaaagctg cctacaccca tagc                                         24

<210> SEQ ID NO 23
<211> LENGTH: 24
<212> TYPE: DNA
<213> ORGANISM: artificial sequence
<220> FEATURE:
<223> OTHER INFORMATION: synthetic

<400> SEQUENCE: 23
agcaaattag tggtctgggc ttgc                                         24

<210> SEQ ID NO 24
<211> LENGTH: 24
<212> TYPE: DNA
<213> ORGANISM: artificial sequence
<220> FEATURE:
<223> OTHER INFORMATION: synthetic

<400> SEQUENCE: 24
ctgaaagctg cctacaccca tagc                                         24

<210> SEQ ID NO 25
<211> LENGTH: 24
<212> TYPE: DNA
<213> ORGANISM: artificial sequence
<220> FEATURE:
<223> OTHER INFORMATION: synthetic

<400> SEQUENCE: 25
aggagtttag tggtctgggc ttgc                                         24

<210> SEQ ID NO 26
```

<211> LENGTH: 24
<212> TYPE: DNA
<213> ORGANISM: artificial sequence
<220> FEATURE:
<223> OTHER INFORMATION: synthetic

<400> SEQUENCE: 26
ctgaaagctg cctacaccca tagc                                           24

<210> SEQ ID NO 27
<211> LENGTH: 24
<212> TYPE: DNA
<213> ORGANISM: artificial sequence
<220> FEATURE:
<223> OTHER INFORMATION: synthetic

<400> SEQUENCE: 27
agcagtttag tggtctgggc ttgc                                           24

<210> SEQ ID NO 28
<211> LENGTH: 21
<212> TYPE: DNA
<213> ORGANISM: artificial sequence
<220> FEATURE:
<223> OTHER INFORMATION: synthetic

<400> SEQUENCE: 28
gttctgggac tggtcctggc c                                              21

<210> SEQ ID NO 29
<211> LENGTH: 22
<212> TYPE: DNA
<213> ORGANISM: artificial sequence
<220> FEATURE:
<223> OTHER INFORMATION: synthetic

<400> SEQUENCE: 29
ccagaggcgg attattgcct cc                                             22

<210> SEQ ID NO 30
<211> LENGTH: 21
<212> TYPE: DNA
<213> ORGANISM: artificial sequence
<220> FEATURE:
<223> OTHER INFORMATION: synthetic

<400> SEQUENCE: 30
tgcctccagg agcctggtct g                                              21

<210> SEQ ID NO 31
<211> LENGTH: 18
<212> TYPE: DNA
<213> ORGANISM: artificial sequence
<220> FEATURE:
<223> OTHER INFORMATION: synthetic

<400> SEQUENCE: 31
cagctcccca ggggcagc                                                  18

<210> SEQ ID NO 32
<211> LENGTH: 20
<212> TYPE: DNA
<213> ORGANISM: artificial sequence
<220> FEATURE:
<223> OTHER INFORMATION: synthetic

<400> SEQUENCE: 32
cgtgctggaa agacatggac                                             20

<210> SEQ ID NO 33
<211> LENGTH: 23
<212> TYPE: DNA
<213> ORGANISM: artificial sequence
<220> FEATURE:
<223> OTHER INFORMATION: synthetic

<400> SEQUENCE: 33
actctctcca ctgacaacaa tag                                         23

PEPTIDES DERIVED FROM MYOSIN 19 AND METHODS OF USE THEREOF

RELATED APPLICATIONS

This application is a continuation of U.S. patent application Ser. No. 14/963,635 filed on Dec. 9, 2015, which claims the benefit of priority of United Kingdom Patent Application No. 1421888.7 filed on Dec. 9, 2014. The contents of the above applications are all incorporated by reference as if fully set forth herein in their entirety.

FIELD OF INVENTION

The present invention is directed to; inter alia, peptides derived from myosin 19, compositions comprising same and methods of use thereof including but not limited to assays for assessing mitochondrial function in a cell.

BACKGROUND OF THE INVENTION

Mitochondria are found in almost all eukaryotic cells and play a role in processes such as ATP production, calcium homeostasis, lipid synthesis and apoptosis signaling. Mitochondria are organized as a network that undergoes constant events of fission and fusion, processes which are critical for their cellular function. The mitochondrial network is sensitive to changes in physiological conditions, as reflected in morphological rearrangements such as hyperfusion in response to starvation and fragmentation in response to oxidative stress.

Additionally, individual mitochondria respond to various cues by changing their intracellular positioning. Mitochondrial motility is primarily based on microtubules (MT), utilizing plus end-directed kinesin motors and the minus end-directed dynein (Pilling. A. D., et al., Mol Biol Cell, 2006. 17(4): p. 2057-68). Actin involvement in mitochondrial motility was suggested long ago, when it was shown that mitochondria enter the apical microvilli of the lower malpighian tube of *Rhodnius Prolixus* in an actin, but not microtubule dependent manner (Bradley, T. J. and P. Satir, J Supramol Struct, 1979. 12(2): p. 165-75).

In neurons, mitochondria move in axons bidirectionally on MTs at speeds reaching ~1 μm/sec with several arrests between runs. Actin depolymerization increases mitochondria speed, suggesting that mitochondria interact with the actin cytoskeleton with opposing effect (Morris, R. L. and P. J. Hollenbeck, J Cell Biol, 1995. 131(5): p. 1315-26). Depolymerization of MTs reduces mitochondrial speed, which is completely halted when both MTs and actin are depolymerized indicating that actin can support mitochondrial movement.

Myosins play a role in key processes such as muscle contraction, cell division, membrane trafficking, endocytosis, tension sensing and dynamic tethers (Hartman, M. A. and J. A. Spudich, J Cell Sci, 2012. 125(Pt 7): p. 1627-32; Woolner, S. and W. M. Bement. Trends Cell Biol, 2009. 19(6): p. 245-52). There are 35 classes of myosins across all eukaryotes and specifically 12 classes in humans.

Myosin 19 was recently discovered as novel mitochondria localized myosin in vertebrates. The motor domain of human myosin 19 shares ~35% identity with other motor domains of human myosins, whereas the tail domain has no obvious homology to other human myosins (Quintero, O. A., et al., Curr Biol, 2009. 19(23): p. 2008-13). Overexpressed myosin 19 tail localizes to mitochondria, indicating that the mitochondrial targeting signal is located within residues 824-970. Overexpression of myosin 19 almost doubled mitochondrial motility while overexpression of the dominant negative tail reduced mitochondrial run lengths, indicating that myosin 19 can modulate mitochondrial motility. Myosin 19 also affected mitochondrial shape, causing mitochondria to assume a tadpole shape with a wider leading edge (Quintero et al., 2009, ibid.).

The mode by which myosin 19 interacts with the mitochondria is unknown. There is a need for peptides capable of targeting and/or delivering compounds to mitochondria in a cell.

SUMMARY OF THE INVENTION

The present invention provides peptides derived from myosin 19 and compositions comprising same. The present invention further provides methods for targeting and/or delivering compounds to mitochondria in a cell, including but not limited to, for diagnosing a mitochondria associated disease or disorder.

In one aspect, the present invention provides an isolated peptide of 5-40 amino acids comprising an amino acid sequence as set forth in SEQ ID NO: 1 (WX$_1$LGLVLANTAMGVGSF), wherein X$_1$ is Pro ("P") or Val ("V"), or an analog, a derivative or fragment thereof.

In another embodiment, there is provided a composition comprising the isolated peptide of the present invention and a carrier. In another embodiment, there is provided a composition comprising the isolated peptide of the present invention and a molecule. In another embodiment, said molecule is a tag selected from the group consisting of a peptide, nucleic acid, a fluorophore, a chromophore, a chemilluminescent molecule, a magnetic particle, a dye and a radioactive isotope.

In another embodiment, there is provided a composition comprising the isolated peptide of the present invention and mitochondria.

In some embodiments, said peptide has an amino acid sequence selected from the group consisting of:

```
                                          SEQ ID NO: 2
(WPLGLVLANTAMGVGSF);

SEQ ID NO: 3
(IIRLWPLGLVLANTAMGVGSFQRKLVVWACL);
and

SEQ ID NO: 4
(LLEAIIRLWPLGLVLANTAMGVGSFQRKLVVWACLQL).
```

In another embodiment, said peptide has an amino acid sequence selected from the group consisting of:

```
                                          SEQ ID NO: 5
(WVLGLVLANTAMGVGSF);

SEQ ID NO: 6
(IIRLWVLGLVLANTAMGVGSFQRKLVVWACL);
and

SEQ ID NO: 7
(LLEAIIRLWVLGLVLANTAMGVGSFQRKLVVWACLQL).
```

In another aspect, there is provided a method of delivering a molecule to mitochondria of a cell, the method comprising contacting said cell with a conjugate, said conjugate comprising a peptide of the invention and the molecule, thereby delivering said molecule to mitochondria of a cell.

In another aspect, there is provided a method of assessing mitochondrial function in a cell, the method comprising:

(a) contacting said cell with a conjugate, said conjugate comprising the peptide of the invention and a molecule, and (b) determining at least one variation of mitochondrial behavior, wherein the at least one variation of mitochondrial behavior is indicative of mitochondrial function in said cell, thereby assessing mitochondrial function in a cell.

In another embodiment, said at least one variation of mitochondrial behavior is represented by a characteristic selected from the group consisting of mitochondrial dynamics (i.e., fusion and/or fission events), motility, speed, morphology, mitophagy and intercellular distribution.

In another embodiment, said mitochondrial function is selected from the group consisting of: metabolic rate, respiratory rate, proportion of aerobic to anaerobic respiration, apoptosis and calcium homeostasis.

In another embodiment, said method is for diagnosing a mitochondria associated disease or disorder in a subject. In another embodiment, said mitochondria associated disease or disorder is associated with a change in mitochondrial behavior, said mitochondrial behavior is selected from the group consisting of fusion, fission, motility, speed, morphology, mitophagy and intercellular distribution. In another embodiment, said mitochondria associated disease or disorder is a mitochondrial dynamics-related disease.

In another aspect, the invention provides a kit for assessing mitochondrial function in a cell, the kit comprising an isolated peptide of 5-40 amino acids and a molecule, said peptide comprising an amino acid sequence as set forth in SEQ ID NO: 1 (WX$_1$LGLVLANTAMGVGSF), wherein X$_1$ is Pro ("P") or Val ("V"), or an analog, a derivative or fragment thereof.

In another embodiment, said kit further comprises at least one additional component selected from: a tag; a reagent or a buffer for isolating mitochondria; and a reagent for inducing cellular stress conditions.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-E: Endogenous myosin 19 is anchored to the outer mitochondrial membrane (OMM). (1A). Fractionation of post-nuclear supernatant using differential centrifugation. Heavy Mitochondrial Fraction (HMF) was pelleted at 3,000×g$_{av}$, Light Mitochondrial Fraction (LMF) was pelleted at 17,000×g$_{av}$ from the HMF supernatant, Cytosol (Cyt) is the supernatant from the 17,000×g$_{av}$ step. α VDAC and α GAPDH were used as markers for mitochondria and cytosol, respectively. α Myo19 is antibody targeted against myosin 19. (1B). Fractionation of the HMF using self-forming Iodixanol gradient (OptiPrep). Fractions were collected by taking a fixed volume from the top of the gradient following the centrifugation step. VDAC and GRP94 were used as markers for mitochondria and ER, respectively. (1C). Protease protection assay on purified mitochondria using Proteinase K (PK) or Carboxypeptidase Y (CPY). ENDO G was used as a marker for the intermembrane space, indicating that the OMM was left intact. (1D). Extraction of membrane proteins using high salt, carbonate or urea. Purified mitochondria were treated as indicated and then pelleted. Pellet (Pel) and supernatant (Sup). (1E). Detergent extraction by Triton X-114. Purified mitochondria were lysed in 1% Triton X-114, incubated at 37° C. for three min to form micelles and pelleted at 300×g$_{av}$ for three min. The aqueous (Aq) and detergent (Det) phases were collected separately. VDAC and GRP94 were used as control for membrane bound and soluble proteins, respectively.

FIGS. 2A-E: Myosin 19 membrane motif. (2A). Colocalization of myosin 19$^{860-890}$-eGFP or myosin 19$^{824-970(\Delta 860-890)}$-eGFP-with mitochondria. (2B). Analysis of myosin 19 membrane motif. The average hydropathy was calculated by averaging the hydropathy of the residues. The charge was calculated as the sum of the charges at physiological pH. (2C). Colocalization of myosin 19$^{824-970}$-eGFP and mutant variants with mitochondria (MitoTracker) or ER (SRs). Bar is 20 μM. (2D). Equilibrium binding of myosin 19-peptide to vesicles. Peptide containing the motif essential for OMM interaction was assayed for binding to vesicles by fluorescence anisotropy. Titrating vesicles versus peptide exhibits a hyperbolic dependence-binding curve. Circles and squares mark the FA and the Total Fluorescence Intensity (FTI), respectively. Solid and dashed lines are the fitted curves using Eq. 1 described below, for the FA and FTI data, respectively. Peptide concentration was 35 μM (2E). Equilibrium binding of myosin 19-peptide to vesicles as a function of NaCl. Myosin 19 co-purifies with HMF and was resistant to high salt extraction. The binding of our peptide to the vesicles was unaffected by increasing NaCl, with an unchanged slope. Peptide and vesicles concentration were 35 μM each.

FIGS. 5A-B: Mitochondria morphology in response to myosin 19 over-expression. (5A). Mitochondria had three morphologies, tubular (left), perinuclear (middle) and tadpole (right). Cell borders are marked in white. (5B). Quantification of the mitochondrial morphology in cells overexpressing the indicated constructs. N=150 cells in three independent experiments. Solid black and white bars represent the percentage of cells exhibiting tubular or perinuclear mitochondria morphology, respectively.

KD. (20D)—Quantification of filopodia number per cell (Top) and filopodia length (Bottom) from mock or Myo19 KD cells is given as mean±s.d. Filopodia were measured from the base of the fascin-eGFP to its tip. N=500 filopodia from 36 cells from either mock or Myo19 KD cells from three independent experiments for filopodia number per cell. N=900 filopodia from 60 cells from either mock or Myo19 KD cells from three independent experiments for filopodia length. The difference was found to be statistically significant using one tailed t-test, **P<0.0001. Error bars are given as s.d. (20E)—Quantification of filopodia length distribution between WT transfected with mock RNAi, Myo19 RNAi and Myo19 KD cells rescued with ectopic expression of Myo19-Halo. (20F)—Mitochondria were found in filopodia of mock treated cells in response to starvation (arrow). Bar is 10 μm (20G)—Patches of Fascin-eGFP could be seen at the cell periphery in response to starvation only in Myo19 KD cells. Bar is 10 μm. (20**H)—Mitochondria distribution was evaluated in Myo19 KD or mock treated U2OS cells showing unchanged distribution of mitochondria. Blue— nuclei, red—mitochondria.

Figure 21A:
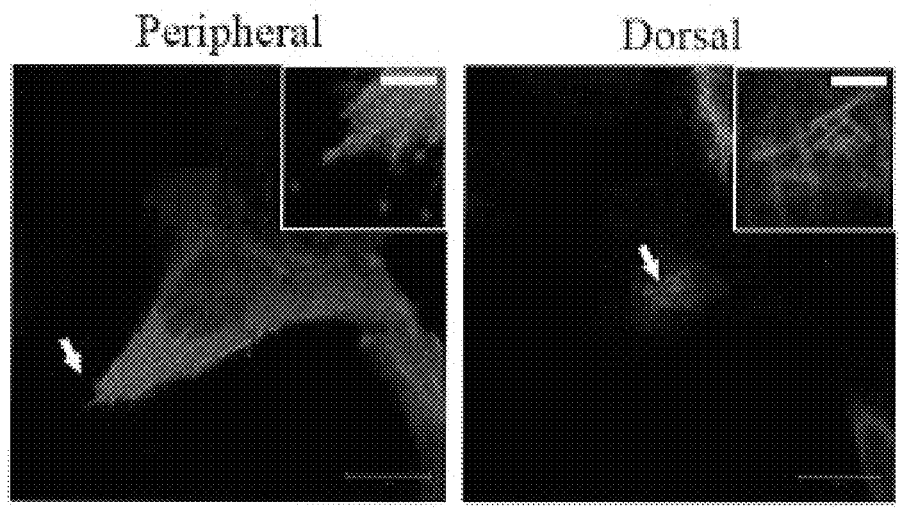
Figure 21B:
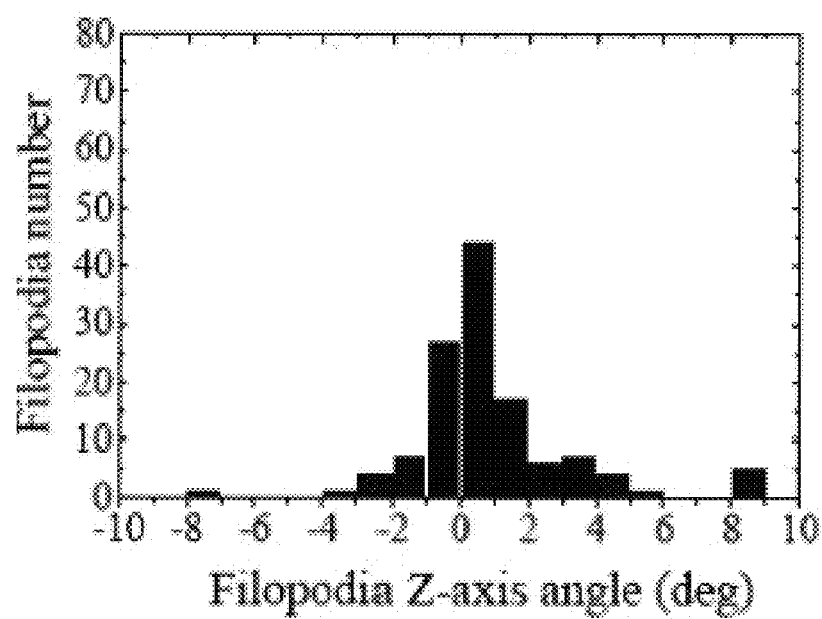
Figure 21C:
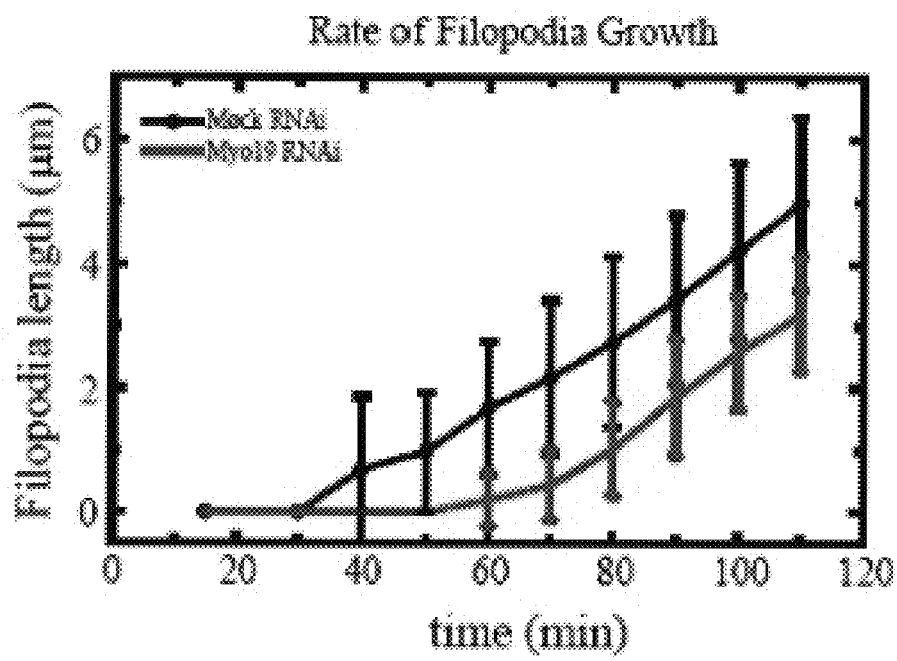

FIGS. 21A-C: Analysis of filopodia formation. (21A)— Myo19-Halo and Fascin-eGFP expressing cells were starved and Z-stack images were collected, revealing that Myo19 localized to tips of peripheral filopodia but not apical filopodia. (21B)—Analysis of the angle of peripheral filopodia. Fascin-eGFP expressing cells were starved and Z-stack images were taken. The peripheral filopodia angle was calculated using Imaris V8.0.0 (21C)—The rate of filopodia formation was measured by performing time-lapse imaging of starved mock or myo19 RNAi transfected U2OS cells expressing Fascin-eGFP and plotting the length of filopodia over time. N=30 filopodia from each group, no statistical difference was found using a one-sided t-test.

Figure 22:
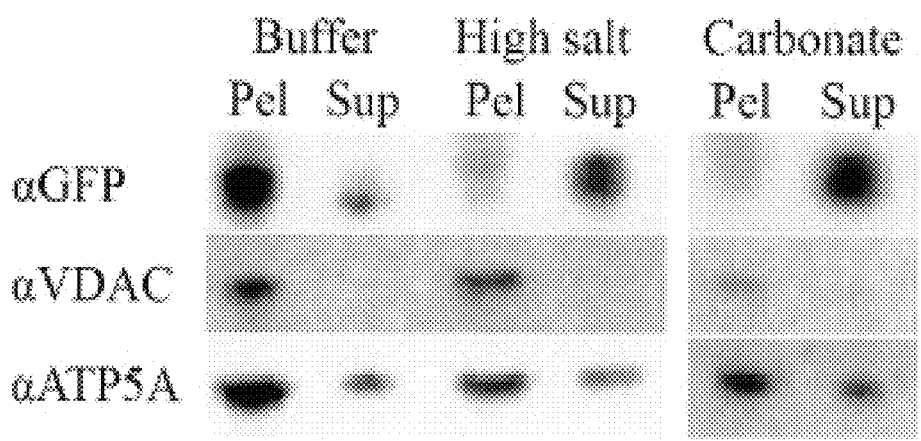

FIG. 22: Myo19 membrane motif. Extraction of membrane proteins using high salt or carbonate. Mitochondria were purified from Myo19860-890-eGFP expressing cells and treated as indicated in materials and methods. Membranes were separated by centrifugation and resolved on SDS-PAGE, Pellet (Pel) and supernatant (Sup).

Figure 23:
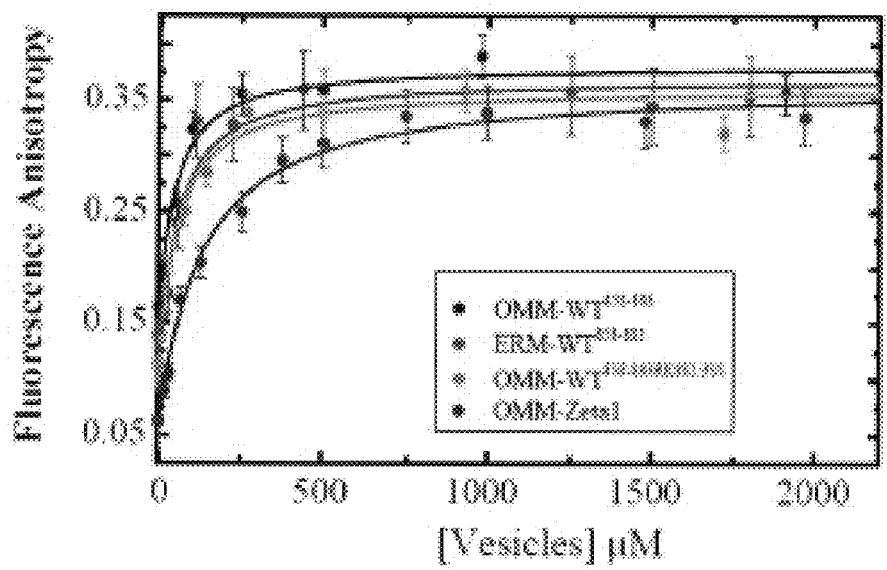

FIG. 23: Myo19 membrane motif. Equilibrium binding of Myo19 and Zeta1 peptides to SUVs (small unilamellar vesicles). Peptides containing the shorter peptide derived from Myo19 membrane motif that contains the peak in predicted helix propensity (Myo19858-883), corresponding ER mutant (Myo19858-883 RK882/3SS) and a hydrophilic peptide (Zeta1) were assayed for binding to ER or OMM mimicking vesicles by FA. Titrating vesicles versus peptide exhibits a hyperbolic dependence-binding curves. Lines are the globally fitted curves using Eq. 3 for the FA and FTI. Peptide concentrations were 4 μM. N=1. Error bars are s.d. of measurements.

Figure 24:
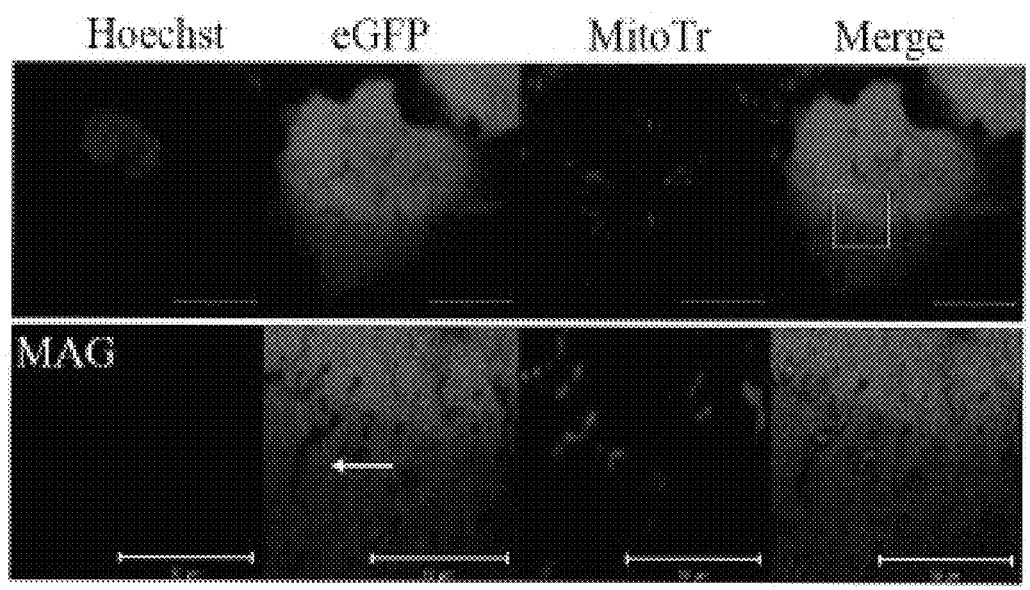

FIG. 24: Bioinformatics analysis of Myo19 predicted membrane motif and Co-localization of myo19-eGFP$^{824-970}$ mutated in the membrane motif (K883S or R882S) with the ER. Co-localization of eGFP with mitochondria. Lower panel is a magnification of the white box from the top panel. White arrow emphasizes lack of localization. Blue—nuclei, green—eGFP, red—mitochondria.

DETAILED DESCRIPTION OF THE INVENTION

The present invention provides peptides derived from myosin 19 and compositions comprising same. The present invention further provides methods for targeting and/or delivering compounds or molecules to mitochondria in a cell, including but not limited to, for diagnosing a mitochondria associated disease or disorder.

The present invention is based, in part, on the finding of peptides derived from the tail region of myosin 19, being capable of anchoring mitochondria, and particularly the outer mitochondrial membrane (OMM). The anchoring capability of the peptides is demonstrated herein to be dependent on the hydrophobicity of said peptides and particular residues therein.

The term "anchoring mitochondria" as used herein refers to the capability of a peptide of the present invention to bind to mitochondria. Specifically, "binding" as used herein refers to direct binding to a mitochondria, such as to the outer mitochondrial membrane.

The present invention is based, in part, on finding the interaction, specificity and the molecular architecture of human myosin 19 and the OMM. As exemplified herein below, myosin 19 binds vesicles mimicking the composition of the phospholipids of the OMM with moderate affinity of ~42 μM in a salt concentration independent manner up to 1M NaCl. Furthermore, the physiological response of myosin 19 during starvation in several cell lines was determined, showing translocation of myosin 19 with mitochondria to filopodia like actin protrusion at the cell periphery in an ATPase and an actin-dependent manner. In sum, the results presented herein indicate that myosin 19 plays a critical role in up regulation mitochondria network morphology, and its redistribution to the high-energy demanding regions in the cell.

Mysoin 19 is, in some embodiment, a mammal myosin 19, preferably a human myosin 19. Human myosin 19 has, according to some embodiments an amino acid sequence depicted in Accession No. NP_001157207.1. In some embodiments, a tail region of myosin 19 relates to the amino acid sequence corresponding to amino acids 824-970 of human myosin 19.

According to some embodiments, the present invention provides an isolated peptide of 5-40 amino acids, wherein said peptide comprises an amino acid sequence as set forth in SEQ ID NO: 1 (WX$_1$LGLVLANTAMGVGSF), wherein X$_1$ is Pro ("P") or Val ("V"), or an analog, a derivative or fragment thereof.

According to some embodiments, the present invention provides a composition comprising an isolated peptide of 5-40 amino acids conjugated to at least one molecule, wherein said peptide comprises an amino acid sequence as set forth in SEQ ID NO: 1 (WX$_1$LGLVLANTAMGVGSF), wherein X$_1$ is Pro ("P") or Val ("V"), or an analog, a derivative or fragment thereof.

In some embodiments, said peptide has an amino acid sequence selected from the group consisting of:

```
                                            SEQ ID NO: 2
(WPLGLVLANTAMGVGSF);

SEQ ID NO: 3
(IIRLWPLGLVLANTAMGVGSFQRKLVVWACL);
and

SEQ ID NO: 4
(LLEAIIRLWPLGLVLANTAMGVGSFQRKLVVWACLQL).
```

In another embodiment, said peptide has an amino acid sequence selected from the group consisting of:

(WVLGLVLANTAMGVGSF); SEQ ID NO: 5

(IIRLWVLGLVLANTAMGVGSFQRKLVVWACL); SEQ ID NO: 6
and (LLEAIIRLWVLGLVLANTAMGVGSFQRKLVVWACLQL). SEQ ID NO: 7

The terms "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure.

The present invention further provides fragments, analogs and chemical modifications of the peptides of the present invention as long as they are capable of targeting the mitochondria in a cell, particularly the OMM.

In another embodiment, said peptide has a length of no more than 40 amino acids, no more than 39 amino acids, no more than 38 amino acids, no more than 37 amino acids, no more than 36, no more than 35 amino acids, no more than 34 amino acids, no more than 33 amino acids, no more than 32 amino acids, no more than 31 amino acids, no more than 30 amino acids, no more than 29 amino acids, no more than 28 amino acids, no more than 27 amino acids, no more than 26 amino acids, no more than 25 amino acids, no more than 24 amino acids, no more than 23 amino acids, no more than 22 amino acids, no more than 21 amino acids, or no more than 20 amino acids. Each possibility represents a spate embodiment of the present invention.

In another embodiment, said analog, derivative or fragment has at least 70%, at least 75%, at least 80°%, at least 85% or at least 90% of the hydrophobicity characteristic of SEQ ID NO: 2. In another embodiment, said analog, derivative or fragment has at least 70%, at least 75%, at least 80%, at least 85% or at least 90% of the hydrophobicity characteristic of SEQ ID NO: 3.

Figure 2E:
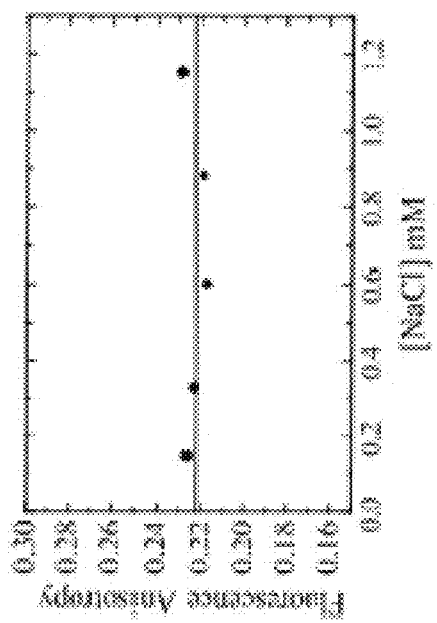

The hydrophobicities and net positive charges of the peptides of the invention are depicted in FIG. 2B. Following is the hydrophobicity analysis of each amino acid residue of SEQ ID NO: 2, from a scale of 1 to 5 wherein 1 is hydrophobic and 5 is hydrophilic: W=3; P=4; L=1; G=3; L=1; V=1; L=1; A=2; N=5; T=3; A=2; M=2; G=3; V=1; G=3; S=3; F=2. Methods for analyzing hydophobicity and net charges of peptides are well known to a skilled artisan.

According to particular embodiments, the arginine at position 882 and/or the lysine at position 883, of human myosin 19 are not substituted with an amino acid having uncharged side chain (e.g., Ser. Thr, Asn or Gin) neither with an amino acid having a negatively charged side chain (e.g., Asp or Glu).

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another: 1) Alanine (A), Serine (S). Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of targeting mitochondria in a cell, as specified herein.

The term "derived from" or "corresponding to" refers to construction of a peptide based on the knowledge of a sequence using any one of the suitable means known to one skilled in the art, e.g. chemical synthesis in accordance with standard protocols in the art. A peptide derived from, or corresponding to amino acid 856-892 of human myosin 19 can be an analog, fragment, conjugate or derivative of a native amino acid 856-892 of human myosin 19, and salts thereof, as long as said peptide retains its ability to target mitochondria in a cell.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefinic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acceylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of targeting mitochondria in a cell as specified herein.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the invention may be synthesized or prepared by techniques well known in the art. The peptides can be synthesized by a solid phase peptide synthesis method of Merrifield (see J. Am. Chem. Soc. 85:2149, 1964). Alternatively, the peptides of the present invention can be synthesized using standard solution methods well known in the art (see, for example, Bodanszky. M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3, 5 dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives, or analogs thereof joined at their amino or carboxy-terminus or at one of the side chains, such as via a peptide bond to an amino acid sequence corresponding to or derived from a different protein. Additionally or alternatively, the peptides of the present invention, derivatives, or analogs thereof can be joined to another moiety such as, for example, a fatty acid, a sugar moiety, and a nucleic acid. Additionally or alternatively, the peptides of the present invention, derivatives, or analogs thereof can be joined to a tagging moiety such as, for example, a fluorophore, a chromophore, a chemiluminescent molecule, a magnetic particle, a dye or a radioactive isotope.

Conjugates comprising peptides of the invention and a protein can be made by protein synthesis, e. g., by use of a peptide synthesizer, or by ligating the appropriate nucleic acid sequences encoding the desired amino acid sequences to each other by methods known in the art, in the proper coding frame, and expressing the conjugate by methods commonly known in the art.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

According to another aspect, the present invention provides an isolated polynucleotide sequence encoding the peptides of the present invention, or an analog or a conjugate thereof, the peptides of the present invention, analog or conjugate thereof capable of targeting the mitochondria in a cell, particularly the OMM.

In another embodiment, there is provided a composition comprising the isolated peptide of the present invention and mitochondria. In some embodiments, said mitochondria is intact mitochondria. In some embodiments, said mitochondria is substantially purified or isolated from other cell components. Methods of purifying mitochondria are known in the art as well as described herein.

In another embodiment, there is provided a composition comprising the isolated peptide of the present invention and a carrier. The term "carrier" refers to a diluent, adjuvant, excipient, or vehicle with which the compound (e.g. the peptide or peptide conjugate described herein) is administered. Such carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Saline solutions and aqueous dextrose and glycerol solutions can also be employed as liquid carriers. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates.

Use of the Peptides

In another aspect, there is provided a method of delivering a molecule to mitochondria of a cell, the method comprising contacting said cell with a conjugate, said conjugate comprising a peptide of the invention and the molecule, thereby delivering said molecule to mitochondria of a cell.

In another embodiment, said method is for visualization of mitochondria in a cell detectable by an assay including but not limited to nuclear imaging (PET or SPECT), or optical imaging, such as by diffuses optical tomography, optical coherence tomography, confocal laser scanning microscopy, fluorescence correlation microscopy, fluorescence resonance energy transfer, or fluorescence lifetime imaging. In one embodiment, said visualization is by means of confocal microscopy.

In another aspect, there is provided a method of assessing mitochondrial function in a cell, the method comprising:
(a) contacting said cell with a conjugate, said conjugate comprising a peptide of the invention and a molecule,
(b) determining at least one variation of mitochondrial behavior and/or determining the level or activity of the molecule in the cell.
thereby assessing mitochondrial function in a cell.

In another embodiment, said mitochondria are the outer mitochondrial membrane (OMM).

In another embodiment, said at least one variation of mitochondrial behavior is indicative of mitochondrial function in said cell. In another embodiment, said at least one variation of mitochondrial behavior is represented by a characteristic selected from the group consisting of mitochondrial dynamics (i.e., fusion and/or fission events), constriction, motility, speed, morphology, mitophagy and intercellular distribution.

Mitochondria are dynamic organelles by several criteria. They engage in repeated cycles of fusion and fission, which serve to intermix the lipids and contents of a population of mitochondria. In addition, mitochondria are actively recruited to subcellular sites, such as the axonal and dendritic processes of neurons. As known to one skilled in the art, important to mitochondrial function is their dynamic ability to undergo fusion, fission and move in cells, with defects implicated in many diseases such as neurodegenerative diseases. As such, excessive mitochondrial fragmentation through fission has been implicated in the pathogenesis of diverse human diseases, including neurodegenerative diseases.

As used herein "mitophagy" refers to degradation of mitochondria through autophagy. Autophagy is a process whereby cellular components are degraded by engulfment into autophagosomes. Autophagosomes fuse with lysosomes, which contain hydrolytic enzymes that break down cellular components. During nutrient deprivation, the products can be recycled into more urgently needed molecules. Although autophagy plays a particularly prominent role during starvation, it also appears to have a housekeeping role in maintaining quality control by turning over organelles and degrading protein aggregates.

Several recent findings indicate that mitophagy can selectively degrade defective mitochondria. Mitochondria that are damaged by a laser irradiation in hepatocytes are selectively removed by mitophagy. Studies in pancreatic β-cells and COS7 cells show that mitochondrial fission can yield uneven products, with one depolarized daughter mitochondrion and one hyperpolarized mitochondrion. Such depolarized mitochondria are much less likely to fuse, have reduced levels of OPA1 protein, and are eventually autophagocytosed. This mitophagy is typically dependent on loss of fusion and the presence of fission.

As used herein, mitochondrial "motility" refers to mitochondrial movement within a cell. Motility of mitochondria is another aspect of mitochondrial dynamics beyond fusion and fission. This aspect is critically important in highly polarized cells, such as neurons, which require mitochondria at sites distant from the cell body, but can also be crucial to cellular function in smaller cells. Defects in both fusion and fission have been shown to decrease mitochondrial movement. Presumably, the large tangle of highly interconnected mitochondria in fission-deficient cells prevents efficient movement, especially into small pathways such as neuronal processes. In fusion-deficient cells, the cause of decreased motility is less clear. Empirically, however, fusion-deficient mitochondria display loss of directed movement, instead hovering in a manner reminiscent of Brownian motion. In neurons lacking mitochondrial fusion, both increased mitochondrial diameter due to swelling and aggregations of mitochondria seem to block efficient entry into neurites, resulting in a dearth of mitochondria in axons and dendrites. These defects result in improperly developed neurons or gradual neurodegeneration.

In some embodiments, the methods described herein assess mitochondrial function selected from the group consisting of: metabolic rate, respiratory rate, proportion of aerobic to anaerobic respiration, apoptosis and calcium homeostasis.

In another embodiment, the method disclosed herein further comprises a step of inducing stress conditions. In another embodiment, said stress is starvation-induced stress. Means for inducing stress, including but not limited to starvation, are known to one skilled in the art as well as demonstrated hereinbelow.

In another embodiment, the method disclosed herein comprises the use of a conjugate of the peptide of the invention and a molecule selected from the group consisting of a peptide and nucleic acid, or a tag selected from the group consisting of a fluorophore, a chromophore, a chemilluminescent molecule, a magnetic particle, a dye and a radioactive isotope. In another embodiment, said conjugate further comprises a linker linking said peptide and said molecule. In another embodiment, said molecule is a mitochondrion.

In some embodiments, there is provided a mitochondria-specific imaging reagent composed of the peptide of the invention as an affinity agent coupled to an imaging agent, being predictive of a mitochondrial-disease or a disease state.

A "disease state" refers to the current status of a disease which may have been previously diagnosed, such prognosis, risk-stratification, assessment of ongoing drug therapy, prediction of outcomes, determining response to therapy, diagnosis of a disease or disease complication, following progression of a disease or providing any information relating to a patient's health status over time.

In another embodiment, said method is for diagnosing mitochondria associated disease or disorder in a subject. In another embodiment, said mitochondria associated disease or disorder is associated with a change in mitochondrial behavior, said mitochondrial behavior is selected from the group consisting of fusion, fission, motility, speed, morphology, mitophagy and intercellular distribution. In another embodiment, said mitochondria associated disease or disorder is a mitochondrial dynamics-related disease.

In another embodiment, said mitochondria associated disease or disorder is a neurodegenerative diseases selected from Parkinson's disease, Alzheimer's disease, Charcot-Marie-Tooth type 2A and Huntington's disease.

In another embodiment, said mitochondria associated disease or disorder is a metabolic disease including but not limited to diabetes (e.g., mitochondrial diabetes, type 1 or type 2 diabetes, diabetes-induced neuropathy) or obesity.

In another embodiment, said mitochondria associated disease or disorder is a cancerous disease. As described in Alirol and Martinou, 2006 (Oncogene, 25, 4706-4716) mitochondrial dysfunction shown by morphological and dynamics changes contribute to cancer progression.

In another embodiment, said mitochondria associated disease or disorder is a cardiovascular disease such as ischemia, reperfusion injury, heart failure, or heart disease.

In another embodiment, the present invention provides a kit for assessing mitochondrial function in a cell, the kit comprising:

a. an isolated peptide of 5-40 amino acids comprising an amino acid sequence as set forth in SEQ ID NO: 1 (WX$_1$LGLVLANTAMGVGSF), wherein X$_1$ is Pro ("P") or Val ("V"), or an analog, a derivative or fragment thereof, or a composition comprising said peptide; and b. at least one signal producing label.

In some embodiments the peptide of said kit is conjugated directly or indirectly to the signal producing label, such as a tag, as described herein.

In another embodiment, the kit comprises at least one of a reagent or a buffer for processing a sample or a reagent or a buffer for isolating mitochondria.

In another embodiment, the kit comprises at least one reagent for inducing cellular stress conditions, e.g., starvation-induced stress. In another embodiment, the kit comprises a starvation medium, such as a glucose-free medium.

In some embodiments the kit further comprises instructions for use of said kit.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes 1-Ill Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA". Scientific American Books, New York; Birren et al. (eds) "Genome Analysis: A Laboratory Manual Series", Vols. 1-4. Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney. Wiley-Liss, N.Y. (1994), Third Edition; "Current Protocols in Immunology" Volumes I-II Coligan J. E., ed. (1994); Stites et al. (eds). "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials & Methods

Myosin 19 Cloning and Plasmids:

Myosin 19 was cloned from an EST library (NIH) cDNA. The amplified PCR product was missing the region encompassing nucleotides 1318-1916 (database sequence FLJ22865). Therefore, this region has been artificially synthesized and cloned to pFC14K (Promega). Myosin 19 full length and its tail domain (residues 824-970) were subcloned to '-N1b using restriction enzymes. The primers used for the cloning are listed in the following table.

Generation of peGFP-myosin 19 mutations and truncations were performed using high fidelity PCR enzymes with phosphorylated primers (Phusion, T4 PNK, NEB). We used peGFP-myosin 19 (peGFP-N1b was kindly provided by Dr. Ayoub (Technion-IIT)) or peGFP-myosin 19 tail (aa 824-970) as template with a single exception for peGFP-myosin $19^{860-890}$ where peGFP-myosin $19^{860-970}$ was used. The products were ligated using T4 ligase (NEB, Promega) and sequenced.

TABLE 1 primers used for the cloning of Myo 19 derived peptides

| Construct | Primers | SEQ ID NO: |
|---|---|---|
| peGFP-Myo19 860-970 | 5'-CATGGCGATCGCTAGCGGAT<br>5'-ATAATCCGCCTCTGGCCCCTG | 16<br>17 |
| peGFP-Myo19 824-890 | 5'-GAGGCAAGCCCAGACCACTA<br>5'-GGCGAACAAAAGCTTCGAATT | 18<br>19 |
| peGFP-Myo19 860-890 | 5'-GAGGCAAGCCCAGACCACTA<br>5'-GGCGAACAAAAGCTTCGAATT | 20<br>21 |
| peGFP-Myo19 R882S | 5'-CTGAAAGCTGCCTACACCCATAGC<br>5'-AGCAAATTAGTGGTCTGGGCTTGC | 22<br>23 |
| peGFP-Myo19 K883S | 5'-CTGAAAGCTGCCTACACCCATAGC<br>5'-AGGAGTTTAGTGGTCTGGGCTTGC | 24<br>25 |
| peGFP-Myo19 RK882SS | 5'-CTGAAAGCTGCCTACACCCATAGC<br>5'-AGCAGTTTAGTGGTCTGGGCTTGC | 26<br>27 |

TABLE 1 -continued primers used for the cloning of Myo 19 derived peptides

| Construct | Primers | SEQ ID NO: |
|---|---|---|
| peGFP-Myo19 P865V | 5'-GTTCTGGGACTGGTCCTGGCC<br>5'-CCAGAGGCGGATTATTGCCTCC | 28<br>29 |
| peGFP-Myo19 Δ860-890 | 5'-TGCCTCCAGGAGCCTGGTCTG<br>5'-CAGCTCCCCAGGGGCAGC | 30<br>31 |
| peGFP-Myo19 G135R | 5'-CGTGCTGGAAAGACATGGAC<br>5'-ACTCTCTCCACTGACAACAATAG | 39<br>33 |

Cell Culture and Cell Lines:

U2OS cells were grown at 37° C. and 5% $CO_2$ in DMEM supplemented with 10% Fetal calf serum (FCS), 2 mM L-Glutamine, 20 mM Hepes-KOH pH 7.4, 100 U/ml penicillin, 100 µg/ml streptomycin and 0.25 µg/ml amphotericin B. HEK293SF-3F6 (ATCC) were grown in suspension in EX-CELL 293 (Sigma) at 37° C. and 5% $CO_2$.

Starvation Conditions:

Cells were rinsed once and incubated in starvation medium (Glucose free DMEM supplemented with 20 mM Hepes-KOH pH 7.4, 5 mg/ml BSA, 100 U/ml penicillin, 100 µg/ml streptomycin and 0.25 µg/ml amphotericin B). Cytoskeleton interfering drugs (final concentration: 0.2 µM Latrunculin B or 0.75 µg/ml Nocodazole) were first diluted in growth media and then added to the cells.

Purification of Mitochondria:

Cells were harvested by centrifugation at 200×g, washed twice with PBS and once in Homogenization medium (HM: 0.25 M sucrose, 1 mM EDTA, 20 mM HEPES pH 7.4). The pellet was resuspended in HM containing Protease inhibitors (HMPI: 0.1 mM benzamidine, 0.055 mM phenanthroline, 0.01 mM bestatin, 0.02 mM leupeptin, 0.005 mM pepstatin A, 1 mM PMSF) and homogenized using a teflon-glass pestle. The homogenate was centrifuged at 1,000×$g_{av}$ to pellet nuclei. The resulting post-nuclear supernatant was centrifuged for 20 min at 10,000×$g_{av}$ to pellet mitochondria and obtain a heavy mitochondrial fraction (HMF).

Protease Protection Assay:

For CPY digestion, purified mitochondria were washed three times with Mes buffer pH 6 (100 mM MES, 0.25 M Sucrose) to remove protease inhibitors. CarboxyPeptidase Y (CPY) was added at 100 µg/ml and the samples were incubated at 25° C. for two hrs. For Proteinase K (PK) digestion, mitochondria were washed three times with HM to remove protease inhibitors. PK was added at 40 µg/ml and incubated on ice for 30 min. Reactions were terminated by addition of PMSF to 2 mM, centrifugation at 10,000×$g_{av}$ for three min to remove the proteases. Sample buffer was added to the samples and they were resolved by SDS-PAGE Membrane Extraction:

Purified mitochondria were resuspended in one of the following solutions: 100 mM $NaCO_3$ pH 11.5, 2 M NaCl in HM, or 2 M urea in 20 mM MES pH 6.5 for 30 min on ice. The samples were then centrifuged for one hr at 150,000×$g_{av}$ in a Sorvall S100-AT3 rotor. The supernatant was collected and the pellet was resuspended in an equal volume of 100 mM HEPES pH 7.4. To perform TCA/Acetone precipitation on $NaCO_3$ and NaCl supernatant, TCA was added to 12% from a 100% stock and allowed to incubate for one hr at 4° C. The samples were centrifuged for 30 min at 17,000×$g_{av}$, resuspended with ice cold acetone and left over night at −20° C. The samples were then centrifuged for 30 min at 17,000×

$g_{av}$, supernatant was removed and the acetone was allowed to evaporate by heating the samples for 10 min at 90° C. Supetnatant containing urea was desalted using Zeba spin desalting columns 7K MWCO according to the manufacturers protocol (Thermo). Sample buffer was added to the samples and they were resolved by SDS-PAGE.

Transfections and Microscopy:

Transfections were performed using Polyethylenimine (PEI). Adherent U2OS cells were plated a day before transfection on plastic or glass bottom dishes and allowed to adhere overnight (ON). Plasmid DNA and PEI were diluted separately in 150 mM NaCl, combined and complex formation was allowed for 25 min at RT before addition to the cells and incubation ON. Hoechst 33342 (0.75 µg/ml Sigma), MitoTracker (30 nM, Molecular probes) and Propidium iodide (1 µg/ml, Sigma) were added 15 min prior to imaging. HaloTag constructs were stained by incubating the cells with HaloTag TMR Ligand ON (25 nM, Promega). The cells were imaged using InCell Analyzer 2000, Confocal Zeiss LSM 700 or Confocal Zeiss LSM 710 in an environmental chamber.

Immunofluorescence:

Cells grown on coverslips were stained with Hoechst, washed with PBS, and fixed with 4% PFA in PBS (EMS) at RT for 15 min. The PFA was removed by washing with PBS, and the cells were blocked for one hr with EZblock. To visualize actin the cells were incubated with Phalloidin 448 (Sigma) for 30 min. The cells were then washed with TBS and mounted on slides using Fluoromount-G (Sigma).

Vesicle Preparation:

Phosphatidylcholine (PC, Sigma), Phosphatidylethanolamine (PE, Sigma), Phosphatidylinositol (PI, Sigma) and Dioleoyl phosphatidylserine (DOPS, Avanti) were mixed in chloroform and evaporated under nitrogen. The vesicles were then resuspended in 40 mM Hepes pH 7.1, 150 mM NaCl and subjected to 10 freeze-thaw cycles in liquid nitrogen and kept in −80° C. The vesicles were thawed and sonicated for five min at low intensity; insoluble material was removed by centrifugation at 100,000×$g_{av}$ for 20 min. Vesicles were used within two days after sonication.

Fluorescence Anisotropy Measurements and $K_D$ Determination:

Equilibrium binding by Fluorescence Anisotropy (FA) measurements was performed with PCI spectrofluorimeter (ISS, Champaign, Ill.) designed as T-format for simultaneous acquisition on two emission channel monochromators equipped with automatic polarizers. Samples were equilibrated (60 min, RT) and then measurements were done with intrinsic fluorescence of the peptide with $\lambda_{ex}$=280 nm using vertical polarized light and the emitted vertical and horizontal polarized light was monitored at 90° with double emission monochromators at $\lambda_{em}$=325 nm. (i-factor for correction of the different gain between the dual PMT detectors was calculated as described by the instrument manufacturer. The binding model for a simple bimolecular reaction was:

$$P + V \underset{}{\overset{K_p}{\rightleftharpoons}} PV;$$

$$K_D = \frac{[P][V]}{[PV]}$$

Under the condition of $P_{tot} \ll K_D$ then the general solution for this equilibrium binding scheme is in the form of the following quadratic equation:

$$[PV] = \frac{(P_{tot} + V_{tot} + K_D) - \sqrt{(P_{tot} + V_{tot} + K_D)^2 - 4P_{tot}V_{tot}}}{2} \quad \text{(Eq. 1)}$$

$P_{tot}$ is monitoring species; $V_{tot}$ is titrating species and [PV] is the bound species. The total fluorescence and anisotropy were fitted globally (Origin Lab 9.0) according to Otto et al. Biophys J, 1994. 67(6): p. 2511-21.

Peptides:

Myo19 peptides were purchased as crude preparations and resuspended in 10% Acetonitrile (ACN) and either 0.1% (for Myo19$^{851-895}$) or 0.01% (for Myo19$^{858-883}$ and Myo19$^{858-RK883SS}$) trifluoroacetic acid (TFA). The peptides were then loaded on a C-18 column (Waters) and separated by reverse phase chromatography. Peaks were analyzed by MALDI-TOF and verified to be of the right molecular weight corresponding to the peptide size. The peptides were then dried and resuspended in either 5% DMF (Myo19$^{858-883}$ and Myo19$^{RK883SS}$) or 16% DMF (Myo19$^{851-895}$) in binding buffer (40 mM Hepes pH 7.1, 150 mM NaCl). Myo19$^{851-895}$, Myo19$^{858-883}$, Myo19$^{858-RK883SS}$ peptides were from GL Biochem (Shanghai, China). Zeta1 was from Sigma (Saint Louis, Mo., USA).

Example 1

Endogenous Myosin 19 Co-Purifies with Mitochondria

Myosin 19 was found to co-localize with the mitochondria in several cell lines and shown to be engaged in mitochondria movements when expressed ectopically (Quintero 2009, ibid.). However, the nature of the physical interaction between myosin 19 and the mitochondria is still unknown.

Mitochondria were purified using differential centrifugation and followed endogenous myosin 19. The results (FIG. 1A) showed that myosin 19 was present only in the heavy mitochondrial fraction (denoted "HMF") but not in the light mitochondrial fraction (denoted "LMF") or in the cytosolic fraction (denoted "Cyt"). When the HMF fraction was further fractionated in a self-forming Iodixanol density gradient, myosin 19 co-fractionated with the mitochondrial marker VDAC, but not with the ER marker GRP94 (FIG. 1B). Noticeably, Western blot analysis did not detect any dissociation of myosin 19 throughout the rigorous purification and fractionation procedure. Therefore, this supports that myosin 19-mitochondria interaction is metastable and highly specific.

Example 2

Myosin 19 is Anchored to the Outer Mitochondrial Membrane (OMM)

The inventors next sought to determine the molecular basis of myosin 19-mitochondria interaction. Several possibilities exist for protein-organelle interactions including sub-mitochondrial localization, interaction via a receptor/mediator protein or direct binding to the outer or inner mitochondrial membrane. The sub-mitochondrial localization of myosin 19 was determined using protease protection assay with Proteinase K (denoted "PK") and Carboxypeptidase Y (denoted "CPY"). With both proteases, myosin 19 was completely digested in the absence of detergents, indicating that it resides on the outer mitochondrial membrane (OMM) with both head and tail protruding to the cytosol. This suggests that myosin 19 doesn't transverse the membrane, otherwise a membrane protected truncated fragment would appear (FIG. 1C).

ENDO G was used as a control to confirm that the degradation was not due to exposure of the intramembrane space (IMS) to the proteases. To address the possibility of protein-protein interactions between myosin 19 and an adaptor protein or OMM receptor, several biochemical extraction methods were utilized on purified mitochondria in an attempt to extract endogenous myosin 19 from the OMM. Interestingly, it was found that myosin 19 can only be extracted from the OMM by carbonate extraction buffer (pH 11.5), whereas myosin 19 was resilient to both high salt (2 M NaCl) and urea (2 M), indicating that the interaction is not electrostatic nor protein mediated (FIG. 1D). Furthermore, the unique properties of detergent phase separation by Triton X-114 showed that myosin 19 was detected only in the detergent phase, whereas the soluble protein GRP94 was found in the aqueous phase (FIG. 1E).

These biochemical findings suggest that myosin 19 is a monotopic membrane protein in which both the N- and C-terminus face the cytosol. The metastable membrane interaction and putative membrane topology are consistent with its possible function as a dynamic link between mitochondria and the actin cytoskeleton. These results indicate that myosin 19 is unlikely to disengage from the mitochondria but rather is being regulated while anchored to the mitochondria, probably by modulations of its ATPase cycle.

Example 3

Residues 860-890 of Myosin 19 Mediate the Interaction with the OMM

Figure 6A:
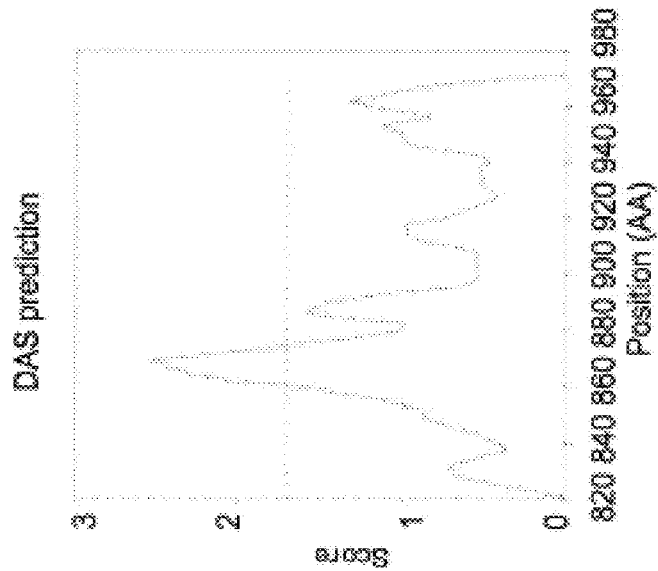
FIGS. 6A-B: Bioinformatic analysis of myosin 19 predicted membrane domain. (6A). Prediction of membrane domain using DAS. (6B). Alpha helix propensity of the predicted membrane domain using MemBrain and helical wheel plot using HeliQuest.

To explore the mode of Myo19-OMM interaction an analysis was performed to identify membrane binding motifs in Myo19 tail domain, which was shown to localize to mitochondria when ectopically expressed. Using DAS prediction webserver, a putative motif was identified between amino acids 860-890 (FIG. 6A). Myo19$^{860-890}$-eGFP was ectopically expressed as the predicated membrane-binding motif and evaluated weather this motif is sufficient to target eGFP to mitochondria (FIG. 2A). To test whether this domain is essential for Myo19 OMM localization a deletion mutant lacking this region (Myo19$^{824-970}$ (Δ860-890)-eGFP) was ectopically expressed. This deletion mutant was distributed mostly throughout the entire cytosol, however not fully excluded from mitochondria (compared to eGFP. FIG. 24). Therefore, a larger deletion, Myo19$^{824-970}$ (Δ851-895)-eGFP, was generated. This mutant was furthermore excluded from mitochondria but not completely. These results strongly support that Myo19$^{860-890}$ motif is both essential and sufficient for OMM localization, however it cannot be excluded that the presence of a minor binding region or other protein-protein region within the tail domain of Myo19 (FIG. 2A). To test whether Myo19$^{860-890}$ membrane motif only dictates OMM targeting or if it is also participating in Myo19 OMM anchorage biochemical extractions were performed on purified mitochondria from cells over-expressing Myo19$^{860-890}$-eGFP.

Figure 6B:
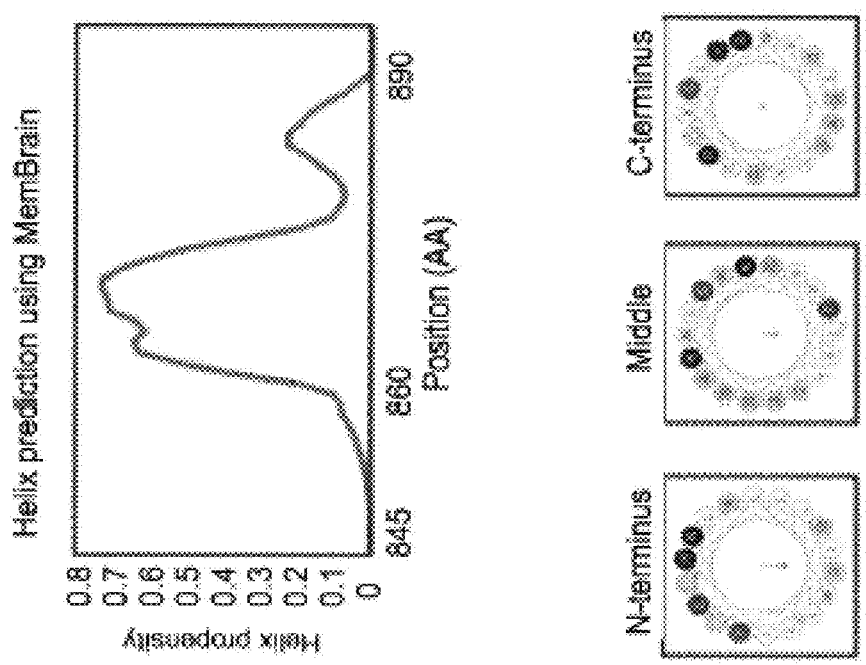
Figure 7:
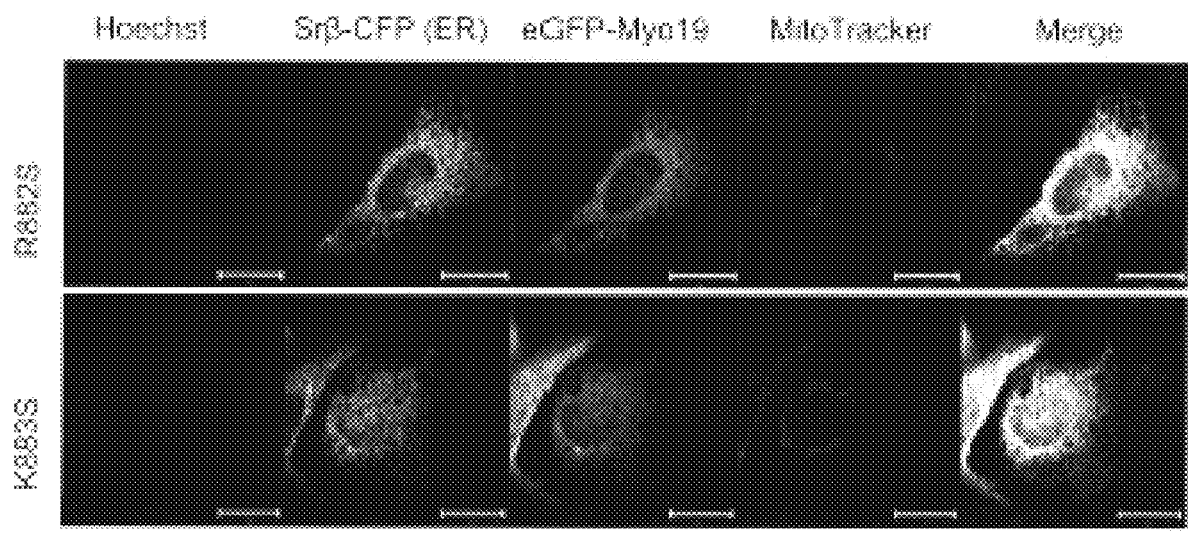
FIG. 7: Co-localization of eGFP fused to myosin 19 tail with the indicated mutations and mitochondria (MitoTracker) or ER (SRβ). Bar is 20 μM.

In accordance to the finding in the cells (FIG. 2A), Myo19$^{860-890}$-eGFP was co-purified with mitochondria, however unlike the endogenous Myo19, it appears to be more sensitive to extraction by salt. Carbonate completely extracts Myo19$^{860-890}$-eGFP from purified mitochondria, similarly to endogenous Myo19 (FIG. 22). The difference in salt sensitivity may be due to insufficient length of the motif to be fully anchored in the membrane as in the WT endogenous protein. Another possibility is that a certain part of Myo19$^{860-890}$-eGFP was correctly anchored, where the rest was present there nonspecifically, e.g. through dimerization of eGFP. Nevertheless, these experiments suggest that this motif is both essential and sufficient for OMM localization. To further explore the OMM targeting the motif sequence was examined. Although there is no consensus sequence targeting proteins to the OMM, it was shown that a moderately hydrophobic motif flanked by positive residues is required for OMM localization. Myo19 membrane motif contains a moderately hydrophobic region between residues 864-880, flanked by basic, positively charged residues (Table 2, flanked by '*'). In order to assess whether Myo19 OMM localization follows these criteria. Point mutations of the basic residues, R882S and K883S, singly (SEQ ID NO: 8 and SEQ ID NO: 9 respectively) or in combination (SEQ ID NO: 10), resulted in a dramatic shift of the intracellular localization of Myo19 to the ER (FIG. 2C, Table 2, FIG. 7). Increasing the hydrophobicity of the hydrophobic region by the point mutation. P865V (SEQ ID NO: 11), resulted in dual localization to both the ER and the mitochondria. Analysis of the P865V mutation shows that the hydrophobicity of the motif increased from 1.141 to 1.482 and may take part in the dual ER/mitochondria localization (FIG. 2C. Table 2). Both results are in accordance with similar studies on tail anchored OMM proteins. In addition, the membrane motif with surrounding residues is predicted to contain two α-helices, 856-878 and 882-892 by MemBrain webserver (FIG. 6B). Plotting this region as a helical wheel using HeliQuest one could observe that the N-terminal portion of the helix has amphiphatic characteristics, which can be found in many membrane-associated proteins (FIG. 6B). Collectively, these results show that Myo19-OMM interaction is highly specific and mutations in this motif dramatically disrupt this interaction.

Example 3 shows that myosin 19-OMM interaction is highly specific and mutations in this motif may disrupt this interaction.

TABLE 2

Myo19 membrane motif and mutations

| Construct | Sequence | SEQ ID NO | Average hydrophobicity | Charge | Localization |
|---|---|---|---|---|---|
| WT | IIRL*WPLGLVLANTAM GVGSF*QRKLVVWACL | 3 | 1.141 | +2 | Mitochondria |
| R882S | IIRL*WPLGLVLANTAM GVGSF*QSKLVVWACL | 8 | 1.141 | +1 | ER |
| K883S | IIRL*WPLGLVLANTAM GVGSF*QRSLVVWACL | 9 | 1.141 | +1 | ER |
| RK882/ 3SS | IIRL*WPLGLVLANTAM GVGSF*QSSLVVWACL | 10 | 1.141 | 0 | ER |
| P865V | IIRL*WVLGLVLANTAM GVGSF*QRKLVVWACL | 11 | 1.482 | +2 | ER/Mitochondria |

The average hydropathy was calculated by averaging the hydropathy of the residues. The charge was calculated as the sum of the charges at physiological pH. The sequence is color-coded to based on hydrophobicity (from most hydrophobic—red, to most basic—blue). Region between "*"

indicates the predicted membrane inserted region. Underlined residues indicates the mutations.

Example 4

Myo19 Derived Peptide Binds to OMM Mimicking Vesicles

Figure 2D:
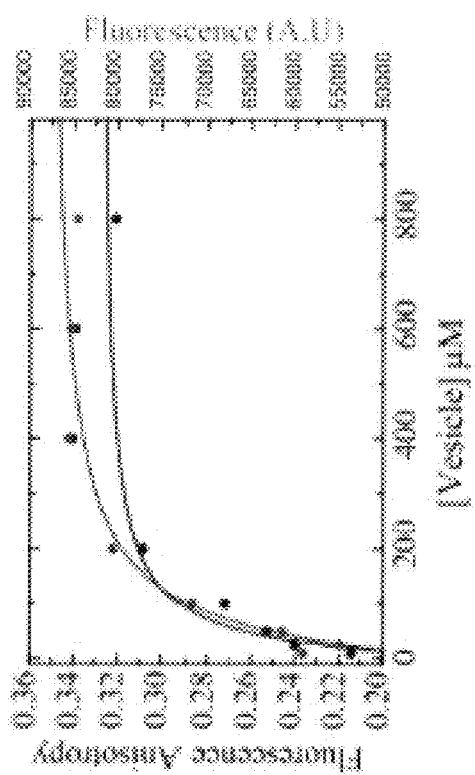

To characterize Myo19 membrane binding motif, the binding of a synthetic peptide representing Myo19 residues 851-895 (SEQ ID NO: 12, Table 3) to lipid SUVs (Small unilamellar vesicles) with a phospholipid composition similar to the OMM (55% PC, 30% PE, 13% PI, 2% DOPS (de Kroon et al., 1997)) was tested. Binding was followed via fluorescence anisotropy (FA) relying on two tryptophan residues that are present in the peptide. The binding of Myo19 peptide to vesicle resulted in both increase in anisotropy and enhanced fluorescence signal (FIG. 2D). Equilibrium binding of Myo19 peptide to vesicles was monitored by titrating peptide versus increasing vesicles concentration. This resulted in a hyperbolic binding curve of both the fluorescence anisotropy (FA) and the fluorescence total intensity (FTI) (FIG. 2D). Therefore, to account for the FTI change during the FA measurements, global fitting to both signals arising from peptide binding to vesicles to compensate for the change in fluorescence yield during FA measurements was applied. Globally fitting the data to a hyperbolic binding equation (Eq. 3) yields an apparent binding constant $K_D=281\pm50$ μM. To verify the results in-vitro that showed that endogenous Myo19 cannot be released from the OMM by high salt, the salt-dependence of the binding interaction between Myo19 peptide and the vesicles was examined. As expected, equilibrium binding of Myo19 peptide to vesicles as a function of [NaCl] up to 1 M exhibits no effect on the magnitude of binding (FIG. 2E, inset, slope≈0), supporting the in-vitro findings (FIG. 1D). Additional binding experiments were performed using a shorter peptide derived from Myo19 membrane motif that contains the peak in predicted helix propensity and the corresponding ER mutant (FIG. 6B, FIG. 35. Myo19$^{858-883}$ (SEQ ID NO: 13 and Myo19$^{858-RK882/3SS}$ (SEQ ID NO: 14), respectively) to either OMM or ER mimicking vesicles (20% PE, 66 & PC, 9% PI, 3% DOPS). Both peptides show similar affinities to OMM mimicking vesicles (45.0±14.1 and 49.0±17.2 μM for WT or mutant peptide, respectively, FIG. 23). The smaller Myo19 derived peptide exhibited tighter affinity than the longer one. This observation may reflect the predicted higher specificity that resides in the shorter peptide than the longer derive peptide. The WT peptide had also a similar affinity to ER mimicking vesicles (50.5±22.0 μM), not showing evident preference to OMM mimicking vesicles. In-vitro binding of a hydrophilic peptide Zeta1 (SEQ ID NO:15, Table 3), was much weaker (~2.5 folds) compared to the Myo19 peptide (124.4±18.7 μM), supporting the notion that Myo19-OMM binding is mediated by hydrophobic interactions (FIG. 23). Although our newly identified membrane motif is essential and sufficient for OMM localization in cells, the cellular specificity may be achieved by unique, yet unidentified cytosolic or others mitochondrial components.

TABLE 3

Peptide used for in-vitro binding

| Peptide | Sequence | SEQ ID NO |
|---|---|---|
| Myo19$^{851-895}$ | PLQTRLLEAIIRLWPLGLVLANTAMGV GSFQRKLVVWACLQLPRG | 12 |
| Myo19$^{858-883}$ | EAIIRLWPLGLVLANTAMGVGSFQRK | 13 |
| Myo19$^{858-RK883SS}$ | EAIIRLWPLGLVLANTAMGVGSFQ<u>SS</u> | 14 |
| Zeta1 | FRWGKPVGKKRRPVKVYPNGAEDESAE AFPLE | 15 |

Example 5

Figure 3C:
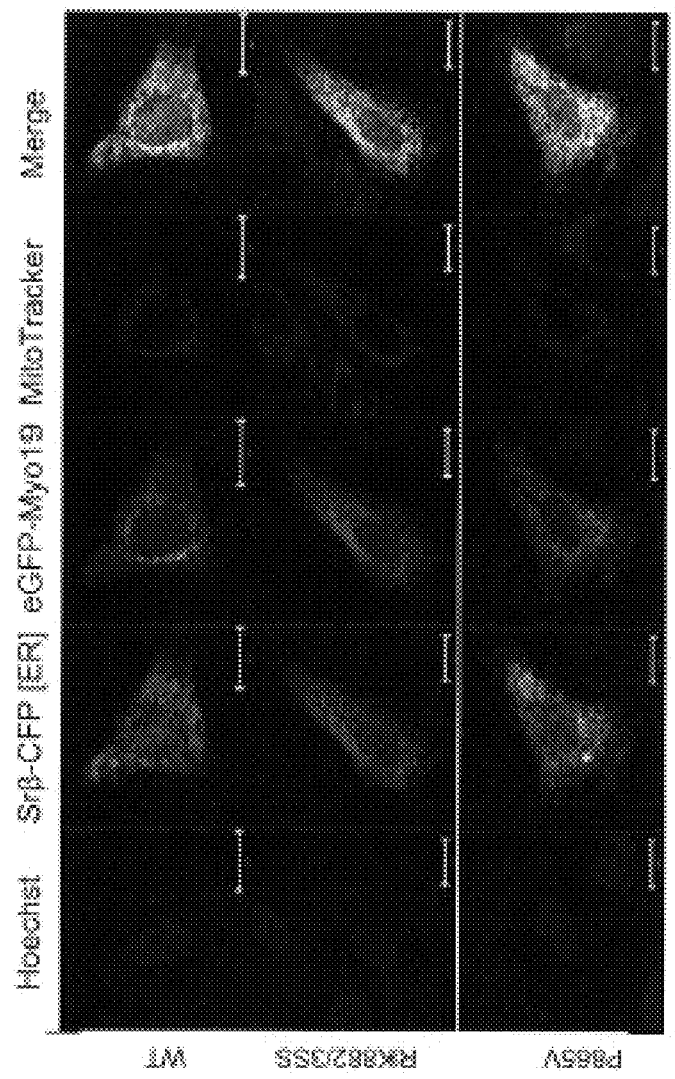
FIGS. 3A-C: Localization of mitochondria and myosin 19 in response to starvation and cytoskeleton interfering drugs. (3A). Localization of mitochondria and the indicated myosin 19 constructs in response to starvation. (3B). Localization of mitochondria and myosin 19 in response to starvation in cells pre-treated with Latrunculin B for 30 min. (3C). Localization of mitochondria and myosin 19 in response to Nocodazole treatment for three hrs. Bar is 20 μm.
Figure 3A:
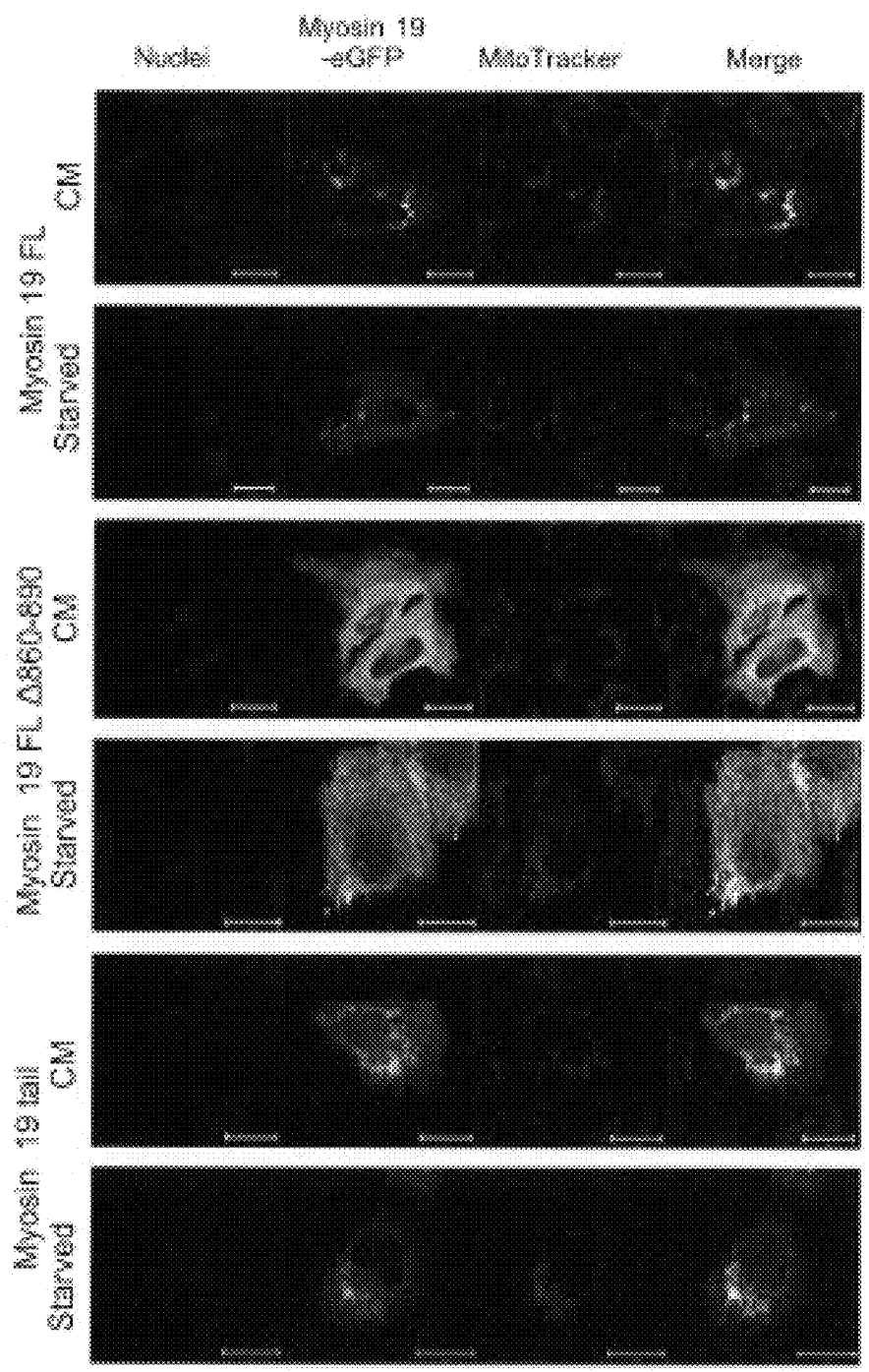
Figure 3B:
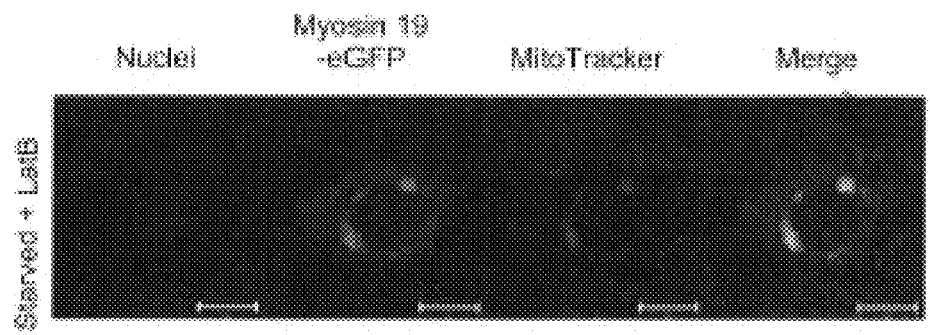
Figure 3C:
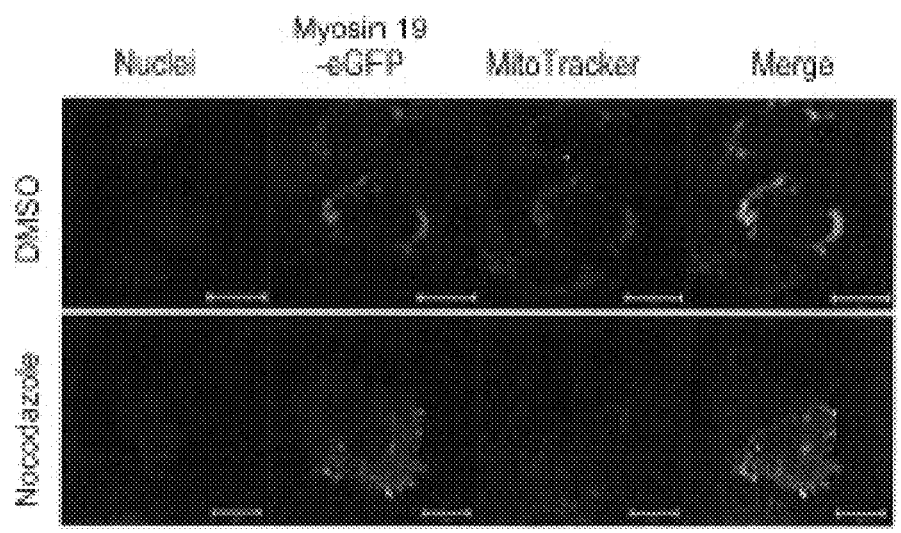
Figure 8:
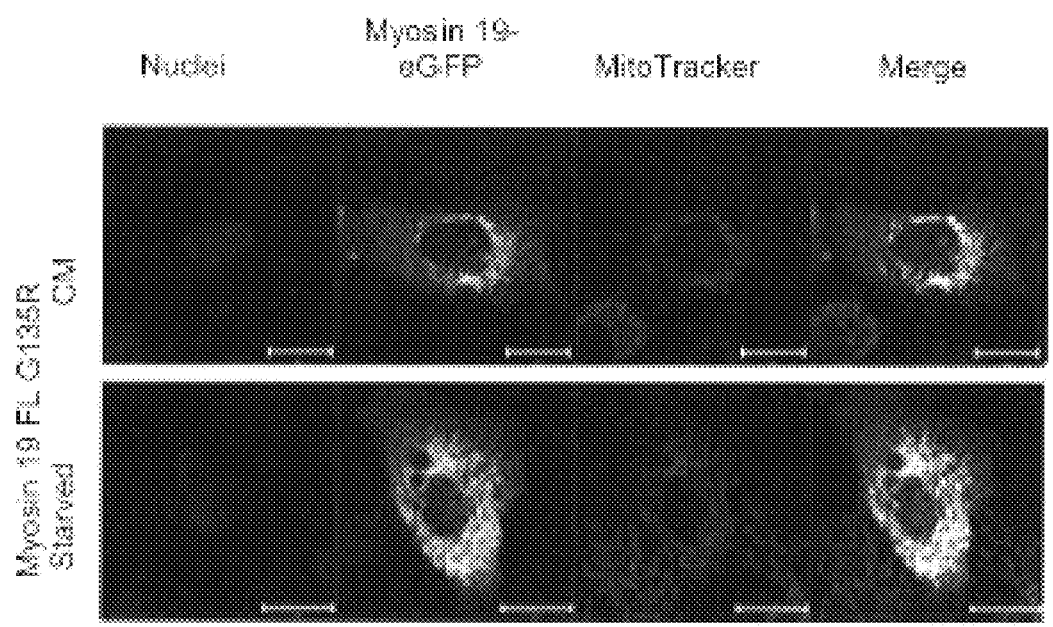
FIG. 8: Localization of mitochondria and the ATPase dead Myosin 19 in response to starvation.
Figure 9:
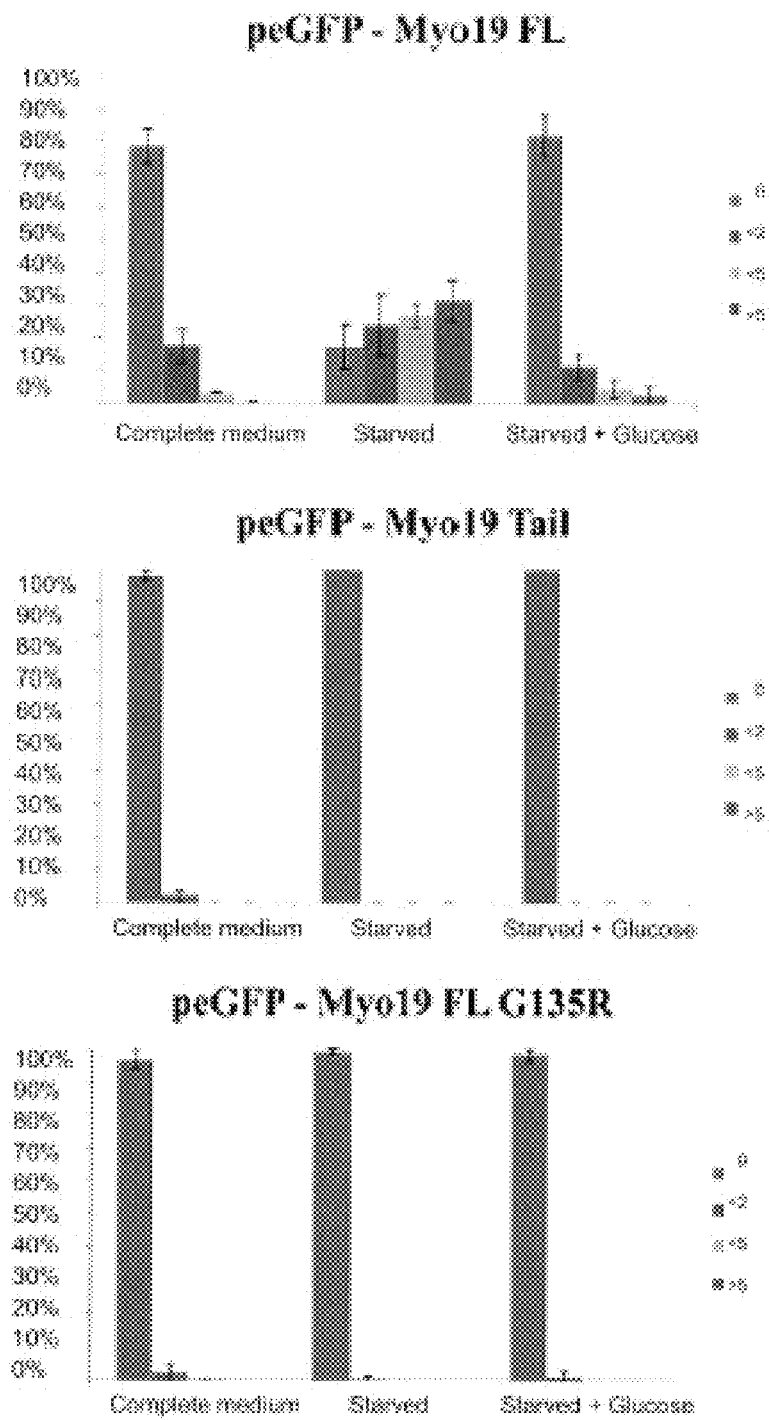
FIG. 9: Quantification of myosin 19 foci in starved cells overexpressing the indicated constructs. Cells were classified as having 0, 1-2, 3-5 or >5 foci per cell. N=150 cells per condition in 3 independent experiments.
Figure 10:
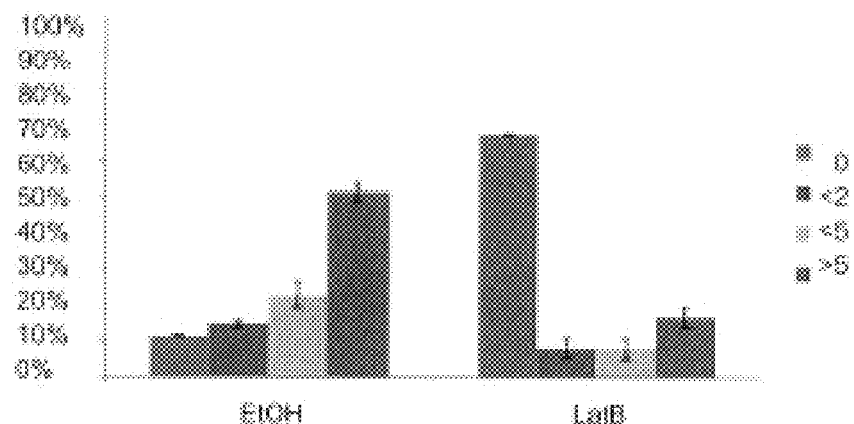
FIG. 10: Quantification of myosin 19 foci in starved cells overexpressing myosin 19 which were pre-treated with 0.2 μM Latrunculin B for 30 min. Cells were classified as having 0, 1-2, 3-5 or >5 foci per cell. N=150 cells per condition in 3 independent experiments.
Figure 11:
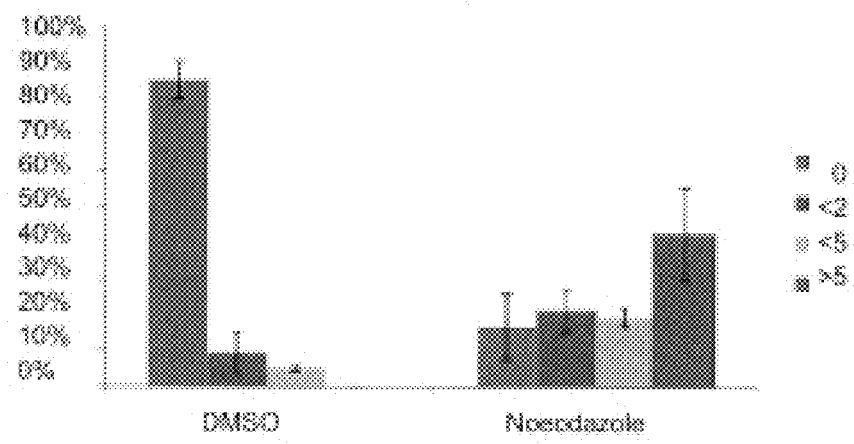
FIG. 11: Quantification of myosin 19 foci in overexpressing myosin 19 which were treated with 0.75 μg/ml nocodazole for three hrs. Cells were classified as having 0, 1-2, 3-5 or >5 foci per cell. N=150 cells per condition in 3 independent experiments.
Figure 12:
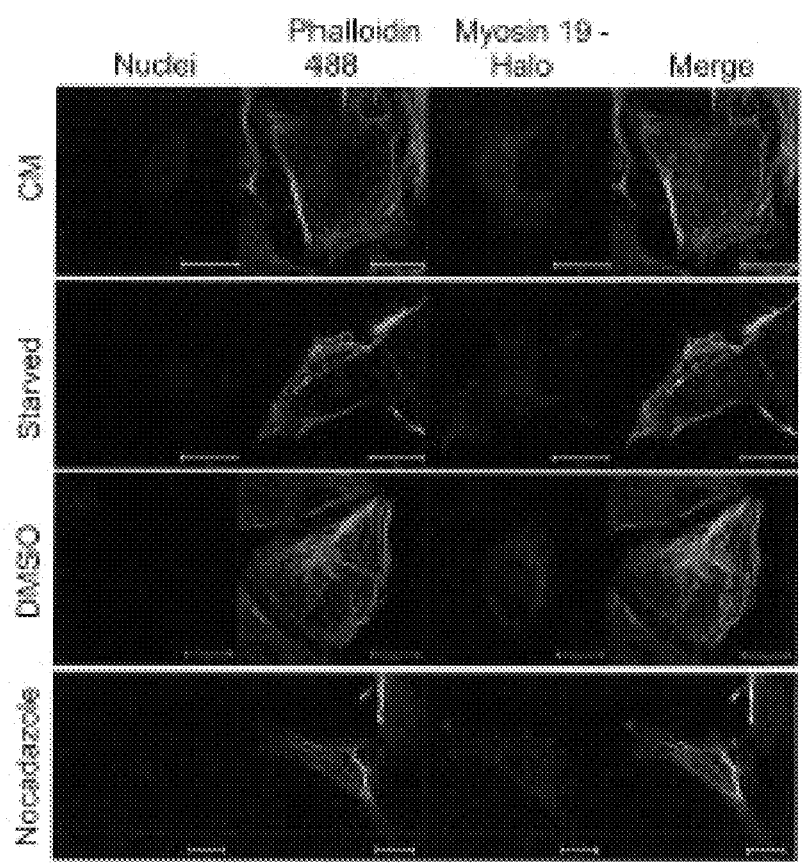
FIG. 12: Co-localization of myosin 19-halo with endogenous actin under starvation or nocodazole treatment. Cells over-expressing myosin 19-halo were fixed and stained with phalloidin.

Starvation Induces Motor-Dependent Migration of Myosin 19 to the Cell Periphery Mitochondria function as an intracellular biosensor that responds to environmental changes, stress cues and physiological stimuli. Therefore, it is essential to test the function of myosin 19 and its relation to mitochondrial distribution and morphology in cells under starvation conditions as well under drugs, which disrupt cytoskeletal structures. Starvation stress was chosen because it strongly shifts mitochondrial dynamics of fission and fusion, inducing hyperfusion of the mitochondrial network, and that fission and fusion depend on force generation on the mitochondria. Therefore, it was assessed whether or not starvation-induced hyperfusion is accompanied by any differential cellular localization of myosin 19. Myosin 19-eGFP was overexpressed and cells were starved for four hrs. Interestingly, starvation had a strong effect on myosin 19 localization to comet-shaped foci and membrane protrusions in the cell periphery together with mitochondria, although some myosin 19 and mitochondria were still present throughout the cells (FIG. 3A, top two panels). The inventors further tested if myosin 19 OMM binding motif is essential for this starvation-induced localization (FIG. 3A, middle two panels). The results show that myosin 19$^{\Delta860-890}$-eGFP does indeed reach the cell periphery, although there is no co-localization of myosin 19$^{\Delta860-890}$-eGFP and the mitochondria throughout the cell, one can still observe some co-localization at the starvation-induced foci, most likely due to endogenous myosin 19. This lends further support to the interpretation that myosin 19$^{\Delta860-890}$-eGFP cannot compete with the endogenous myosin 19 because of its inability to bind the mitochondria. The inventors further assessed whether this transition of myosin 19 to the cell periphery requires myosin 19 motor activity utilizing an overexpression of myosin 19 tail (FIG. 3A, bottom two panels, FIG. 8) and an ATPase dead mutant G 135R (FIG. 9, FIG. 8). Both did not undergo translocation to the cell periphery. Interestingly, these experiments demonstrated a dominant negative effect, preventing the migration of mitochondria to the cell periphery under starvation conditions, most likely competing with endogenous myosin 19. Importantly, supplementation of the starvation medium with glucose abolished the altered localization of both myosin 19 and the mitochondria to the cell periphery, indicating that it is a response to glucose starvation rather than other nutrients. Similar membrane protrusions have been shown to form in other cell lines in response to glucose starvation deprivation. These results demonstrate that under starvation, myosin 19 motor ATPase activity is required for migration of mitochondria to the cell periphery, raising the question for the role of cytoskeletal tracks for this translocation of myosin 19 and the mitochondria. Indeed, pre-treatment of cells with 0.2 μM Latrunculin B that disrupts actin filaments of the cytoskeleton for 30 min inhibited the starvation-induced translocation of myosin 19 and the mitochondria to the cell periphery (FIG. 3B, FIG. 10). Interestingly, nocodazole treatment induced the same altered localization, possibly by activating the small GTPase rhoA, which is involved in initiation of membrane protrusions (FIG. 3C. FIG. 11, FIG. 12). Collectively, these results strongly support the role of myosin 19 in regulating the mitochondrial network both under normal growth conditions and under stress.

Figure 4A:
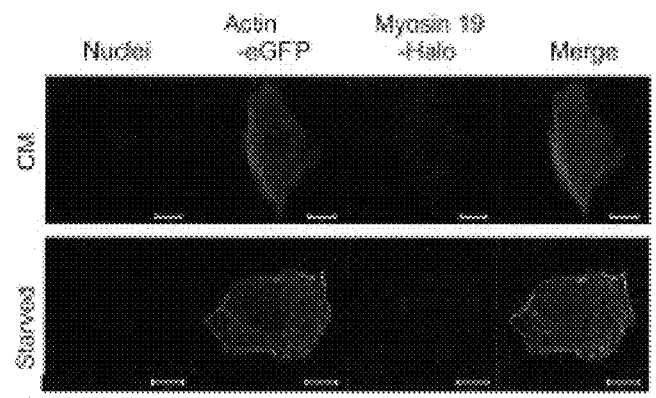
FIGS. 4A-C: Myosin 19 localizes to the tips of actin protrusions in response to starvation. Colocalization of Halo-tagged myosin 19 with (4A) Actin-eGFP. (4B) Paxillin-eGFP or (4C) Vinculin-Emerald in response to starvation. Bar is 20 μm.
Figure 4B:
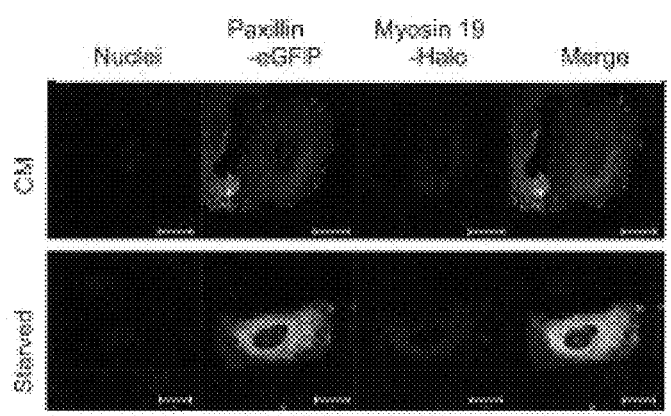

The translocation of mitochondria along with myosin 19 to cell periphery foci raised the possibility that they are required to supply high-energy demand to cytoskeleton remodeling. Since foci formation was dependent upon an active motor and F-actin, it was assessed whether myosin 19 starvation-induced localization coincides with actin protrusion. Myosin 19 localized to the tips of actin protrusions extending away from the cell as seen by co-expression of myosin 19 and GFP-actin or in fixed phalloidin labeled cells (FIG. 4A, FIG. 11). By positioning mitochondria at the tips of the actin protrusions, the high demand for energy required for cell motility, migration and environmental survey, all of which rely on actin network remodeling is met. This is a key finding that all three components, actin, myosin 19 and the mitochondria are localized at the tip of actin protrusions, using the actin filaments, myosin 19 motor activity and membrane-binding motif to translocate mitochondria to the peripheral foci. Several known actin protrusion structures are known, however, filopodia is one of the major actin protrusions extending from the cell. The inventors used focal adhesion and filopodia marker proteins, Paxillin and Vinculin to test whether or not these actin protrusions contain these bona fide markers. Expressing eGFP-Paxillin or Emerald-Vinculin (FIGS. 4B & C) did show partial localization to these actin protrusions, suggesting that these actin protrusions are indeed filopodia. Interestingly, myosin 19 was localized farther towards the tip of the actin protrusion compared to Paxillin and Vinculin.

This example provides a direct link between myosin 19, mitochondria and filopodia formation. Furthermore, this linkage implies that at a specific time myosin 19 and the mitochondria must reach the edge of the filapodia by passing through the paralleled actin bundles of the actin protrusion and the focal adhesion complexes marked by paxillin and vinculin.

Example 6

Myosin 19 Overexpression Affects Mitochondrial Network Distribution

Microarray analyses revealed that myosin 19 expression is increased in certain cancers, when compared to normal tissues. This may display changes in mitochondria dynamics and localization in cancer cells. The inventors therefore hypothesized that myosin 19 overexpression may alter the overall mitochondrial network. Hence, myosin 19 was overexpressed to study the effects on the mitochondrial network morphology and subcellular distribution. The mitochondrial network was mostly tubular and filled the entire cell in untransfected or mock-transfected cells (FIG. 5A, left panel). In contrast, in cells overexpressing myosin 19-eGFP, a dramatic effect on mitochondrial network distribution was observed, being restricted to the perinuclear region (FIG. 5A, middle panel). Overexpressing myosin $19^{824-970}$-eGFP or only the membrane motif myosin $19^{860-890}$-eGFP revealed a perinuclear confinement of mitochondria that was mediated by the tail region spanning residues 824-970 but not only by the membrane motif (FIG. 5B). The full-length construct induced additionally tadpole-like shape mitochondria morphology (FIG. 5A, right panel). The membrane motif (myosin $19^{860-890}$-eGFP) had a mild effect on the mitochondrial morphology, shifting the mitochondria partially to the perinuclear region (FIG. 5A, middle panel). This can be attributed to saturation of the OMM and competition with other anchored and OMM associated proteins that regulate the mitochondrial morphology and distribution. Evidently, the tail (myosin $19^{824-970}$) participates in an additional manner at regulating the mitochondrial morphology, possibly by acting as a docking site for other proteins. Thus, the inventors have indirectly modulated the equilibrium of the mitochondria network in the cell, directing mitochondrial distribution and morphology to be dominated by myosin 19. This further suggests an active role of myosin 19 in the distribution of mitochondrial network and morphology. Myosin 19 contribution to mitochondrial movement is linked directly to actin network. However, it has also been found that actin contributes to mitochondrial dynamics and that disruption of F-actin dampens mitochondrial fission. In addition, disruption of the normal fusion and fission balance has been shown to result in perinuclear mitochondria morphology. Therefore, one cannot exclude the possibility that overexpression of myosin 19 would promote perinuclear distribution of mitochondria by opposing tubular mitochondria organization and modulation of an actin-dependent fission pathway.

The above examples revealed the interaction, specificity and molecular architecture of human myosin 19 with the OMM. The in vitro binding affinities of myosin 19 membrane motif to vesicles mimicking the composition of the phospholipids of the OMM were determined. Myosin 19 bound the vesicles with a moderate affinity of ~42 μM in a salt concentration-independent manner up to 1 M NaCl. Further, the physiological response of myosin 19 during starvation in U2OS cells was determined showing that it translocates with mitochondria to filopodia-like actin protrusions at the cell periphery in an ATPase and an actin-dependent manner. The examples indicate that myosin 19 plays a key role in regulation of mitochondria network morphology, and its redistribution to the high-energy demanding regions in the cell.

Example 7

Figure 13A:
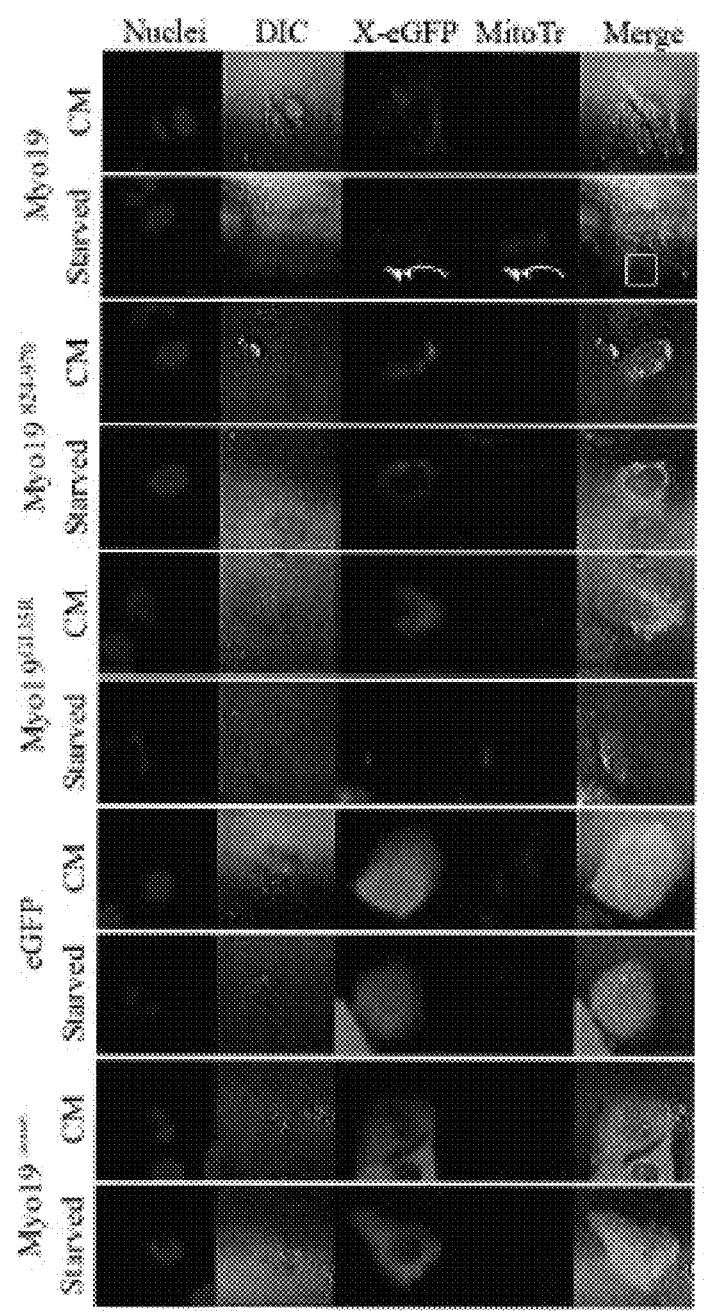
FIGS. 13A-C: Glucose starvation induces mitochondria localization to foci in the cell periphery depends on an active Myo19. (13A). Live imaging of U2OS cells ectopically expression the indicated Myo19 constructs grown in complete medium (CM) or under glucose starvation. White line—outline of a filopodia emphasizing that both Myo19-eGFP and mitochondria are co-localized at filopodia tip. White Arrow—example of Myo19 foci in the cellular protrusions. Mag.—magnification of the white-boxed region showing that Myo19 and mitochondria are present in the foci. (13B). Quantification of foci localization of the indicated Myo19 constructs. Myo19 expressing cells were scored according to the number of foci present under complete medium (containing 25 mM glucose), starvation (No glucose), or starvation medium supplemented with 5.5 mM glucose. Values are presented as percent of cells having the indicated foci number out of total analyzed cells. (13C). Localization of ectopically expressed Myo19 under starvation medium supplemented with 5.5 mM glucose. Note the lack of both peripheral protrusions nor foci localization of Myo19 (compared to row 2 in panel A). Blue—nuclei, DIC—Differential Interference Contrast microscopy, green—eGFP fused Myo19 constructs, MitoTr—mitochondria. Bar is 20 μm, except in magnification where it is 5 μm. N≥150 cells from three independent experiments, error bars are given as s.d.
Figure 13B:
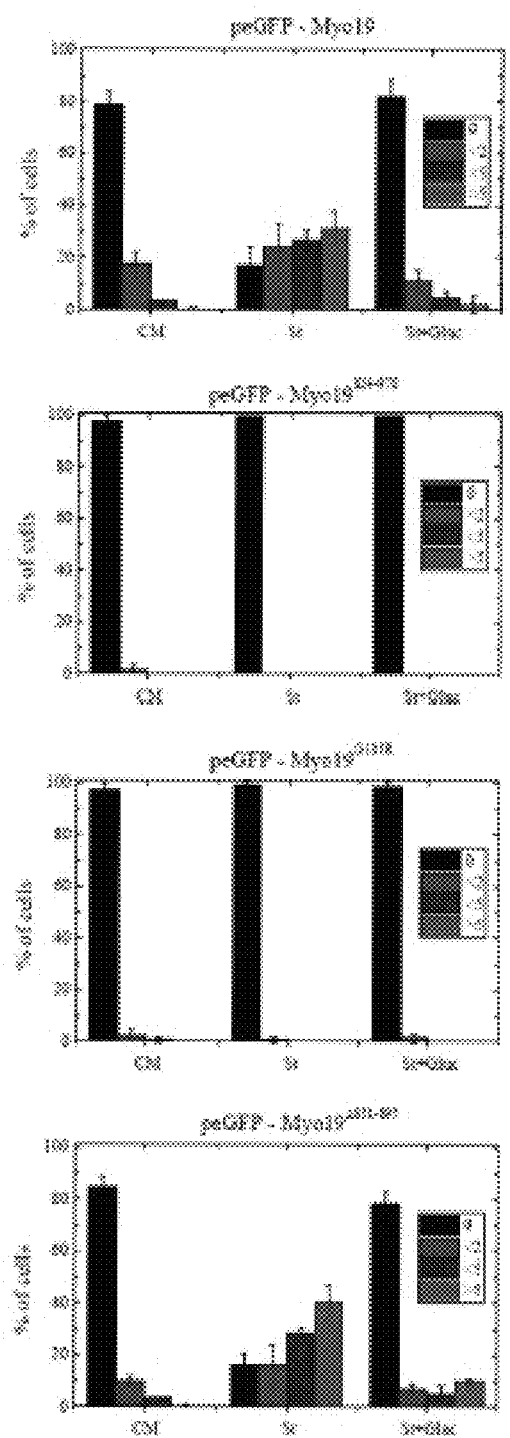
Figure 14A:
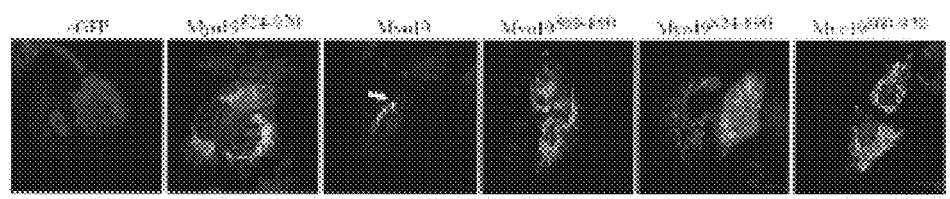
FIGS. 14A-E: Ectopic expression of Myo19 affects mitochondrial network distribution. (14A). Representative images of U2OS cells ectopically expressing eGFP fused Myo19 truncation mutants (Myo19$^{824-970}$-eGFP, Myo19-eGFP, Myo19$^{860-890}$-eGFP, Myo19$^{824-890}$-eGFP, Myo19$^{860-970}$-eGFP), eGFP was used as control. Blue—nuclei, green—eGFP fused Myo19, red—mitochondria. (14B). Quantification of the mitochondrial morphology. Cells were scored as having tubular, intermediate-tubular, intermediate and globular morphology. N≥100 per each construct from three independent experiments. (14C). To verify that the Myo19 mutant constructs are expressed, whole cell lysates were prepared from the ectopically expressing cells and resolved by SDS-PAGE. Expression of the constructs was verified by WB with an αGFP antibody. * indicates non-specific bands. Red box indicate the expressed construct (14D). Image enhancement using Fourier transformation suggesting that globular mitochondria are comprised of a cluster of adjacent mitochondria. (14E). Microirradiation of globular mitochondria using 405 nm laser based on a protocol modified from. Red—globular mitochondria, red box—irradiated box of 0.5×0.5 μm, yellow—region where the mitochondria membrane potential dependent dye MitoTracker intensity was lost. The "before" image was taken prior to the microirradiation, the "after" image was taken immediately after microirradiation. Left—microirradiation of tubular mitochondria to verify that micro-irradiation at 405 nm causes depolarization of mitochondria membrane potential and release of MitoTracker far from the actual microirradiation spot. Right—microirradiation of globular mitochondria.
Figure 14B:
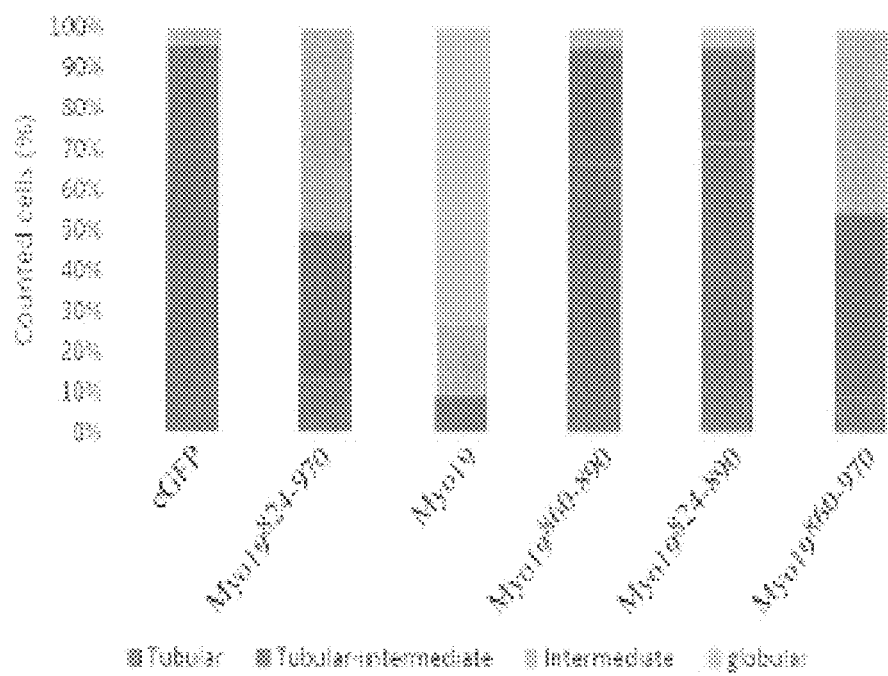

Glucose Starvation Induced Localization of Mitochondria and Myo19 to Foci at Cell Periphery Protrusions Mitochondria function as an intracellular biosensor that responds to environmental changes, stress cues and physiological stimuli hence, it is very intriguing to test Myo19 and its interaction with the mitochondrial network dynamics and morphology in cells under stress such as starvation that induces mitochondrial response. To test this Myo19 fused to eGFP (Myo19-eGFP) was ectopically expressed in U2OS cells. Myo19 and mitochondria localization in response to glucose starvation were examined. Under complete media conditions (CM), Myo19 localizes to mitochondria with some diffuse cytosolic appearance, which may be due to the ectopic expression, similarly to previous works (FIG. 13A-B). Notably, expression of Myo19-eGFP caused mitochondria to clump together into globular structures in a motor dependent manner (FIG. 13A-B and FIG. 14A).

Figure 13C:
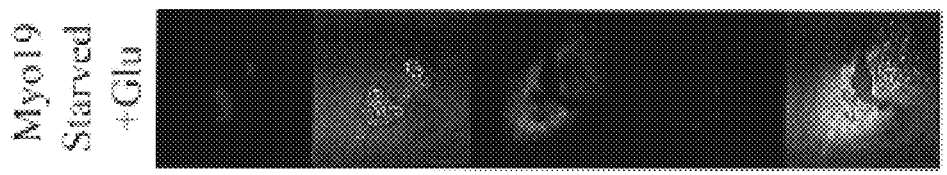
Figure 14C:
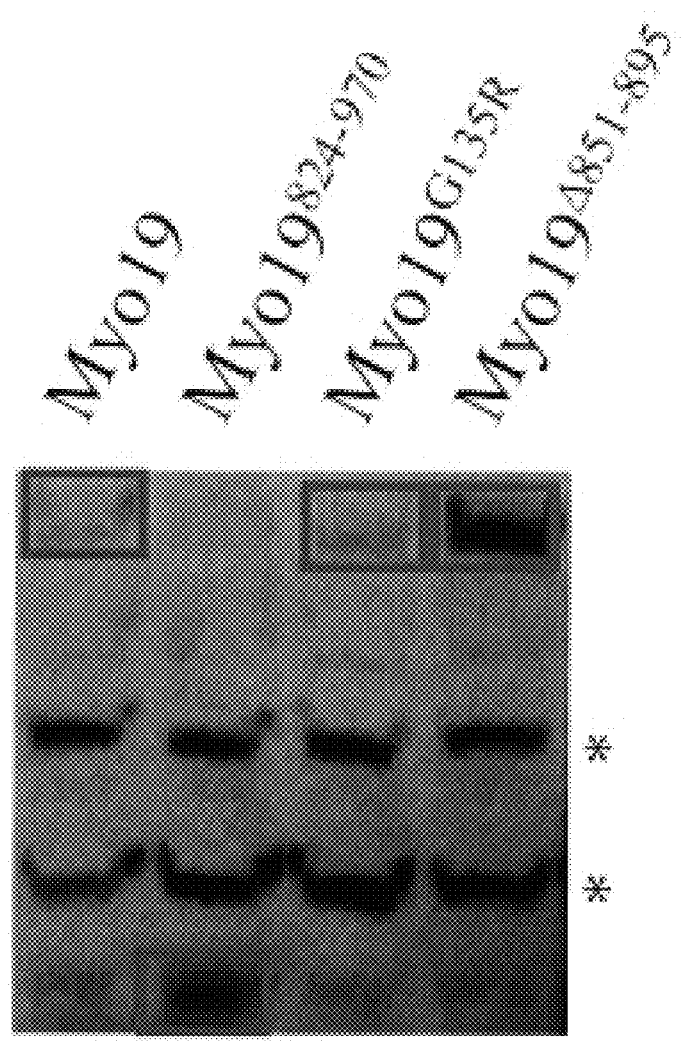
Figure 14D:
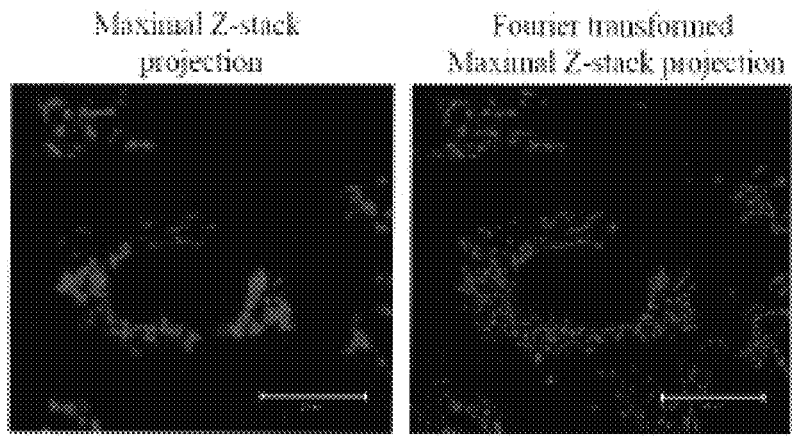
Figure 14E:
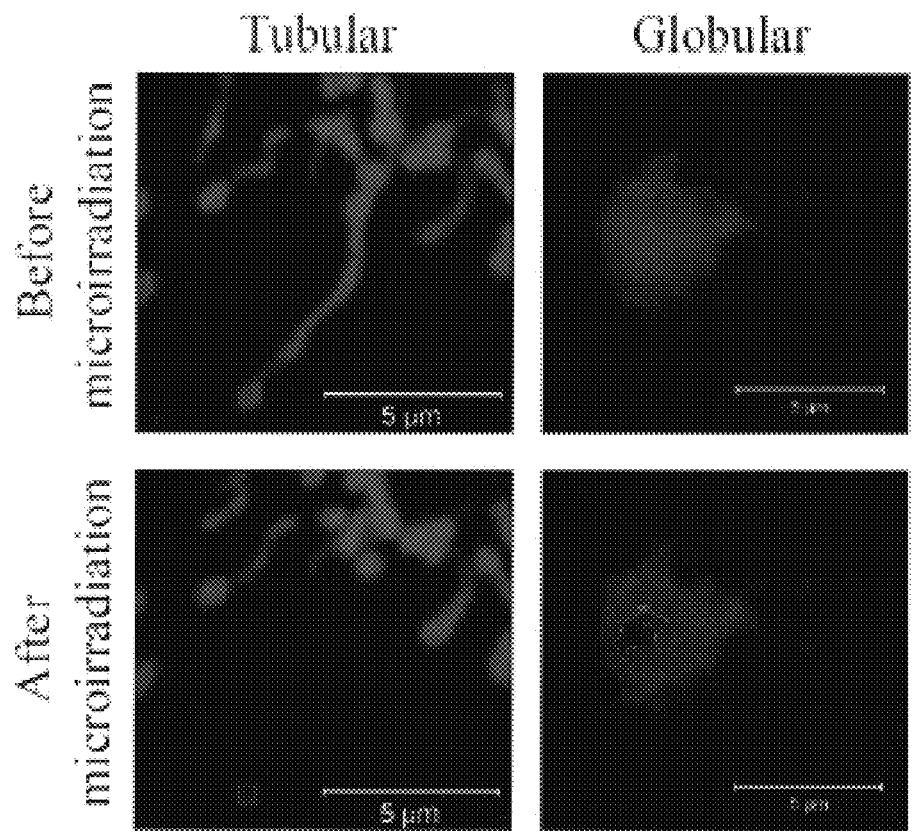

In contrast to CM conditions, glucose starvation of U2OS cells resulted in the localization of Myo19 together with mitochondria to the foci in protrusions extending from the cells (FIG. 13A-B). Quantification of Myo19-eGFP foci revealed that >80% are positive for mitochondria. This was done by calculating the ratio between MitoTracker red stained Myo19-eGFP foci to all Myo19-eGFP foci (FIG. 13A-B, N=160 from 14 cells). Notably, these protrusions formed randomly around the cell periphery, showing no preference of directionality, which is most likely due to missing cues such as mechanical forces or chemotactic molecules. The localization of Myo19 to the starvation-induced foci depended on an active full-length Myo19 (FIG. 13A-B). Neither eGFP alone, Myo19 tail (Myo19$^{824-970}$-eGFP) nor ATPase dead full-length Myo19 (Myo19$^{G135R}$-eGFP) were able to localize to the protrusions, linking Myo19 enzymatic function to protrusion localization. To test whether the localization requires mitochondria binding motif, the experiment was repeated with a cytosolic mutant of Myo19 (Myo19$^{\Delta851-895}$-eGFP), which was able to localize to these protrusions, however, no mitochondria was co-localized with this deletion mutant, demonstrating the requirement for mitochondria binding motif for localization with the mitochondria (FIG. 13A-B). Verification of expression of the Myo19 constructs was performed using WB (FIG. 14C). Supplementation of the starvation medium with glucose completely prevented both protrusions and foci formation, indicating that it is a response to glucose starvation rather than other nutrients (FIG. 13C).

Figure 15:
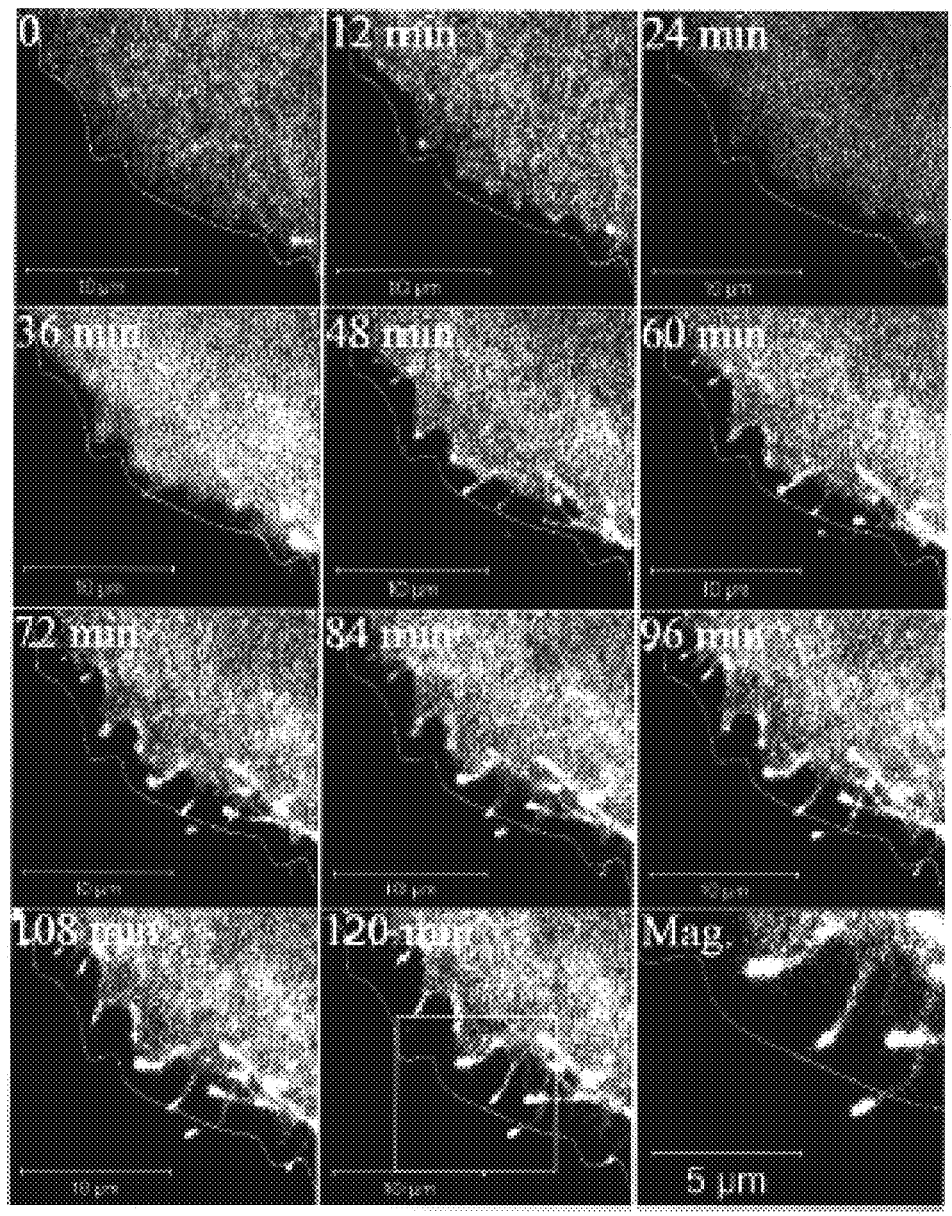
FIG. 15: Live imaging of starvation induced foci localization. Micrographs from time-lapse live imaging of starved cells ectopically expressing myo19-eGFP show formation of Myo19 foci. Note that some of the Myo19 foci are localized within the cell boundaries at the beginning of imaging marked by a yellow line (+20 min of starvation), whilst some foci extend beyond the cell boundary. Mag—magnification of the white-boxed region. Bar is 10 μm except in magnification where it is 5 μm.
Figure 16A:
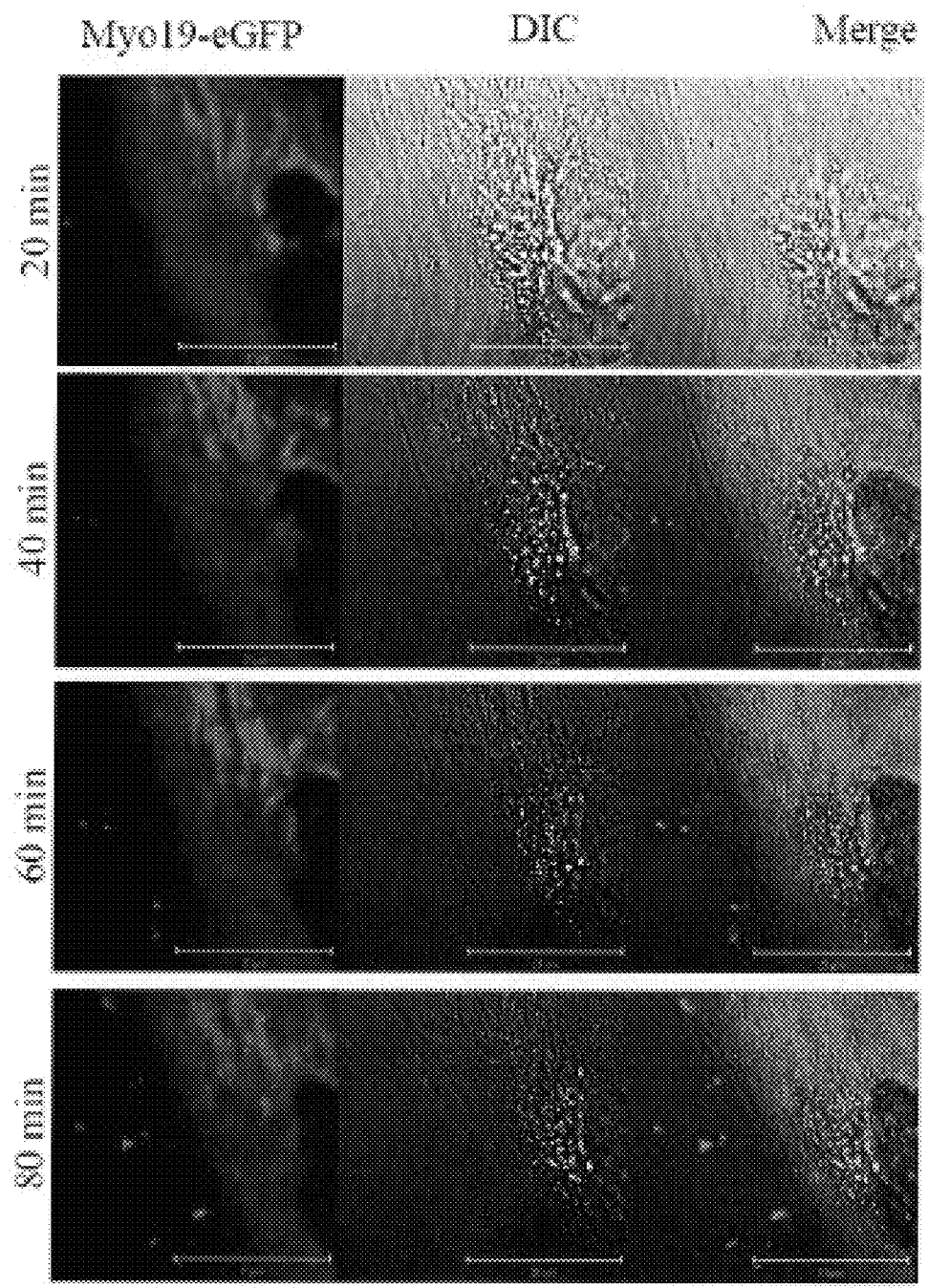
FIGS. 16A-B: Time-lapse live imaging of U2OS cells. (16A). Myo19-eGFP expressing U2OS cells were starved and imaged via time-lapse microscopy. Note the formation of myosin 19 foci at the tips visualized in the DIC channel. (16B). Time-lapse live imaging of WT U2OS cells demonstrating the formation of filopodia over time. Bar is 20 μm. Green-Myo19-eGFP, DIC—differential interference contrast microscopy.
Figure 16B:
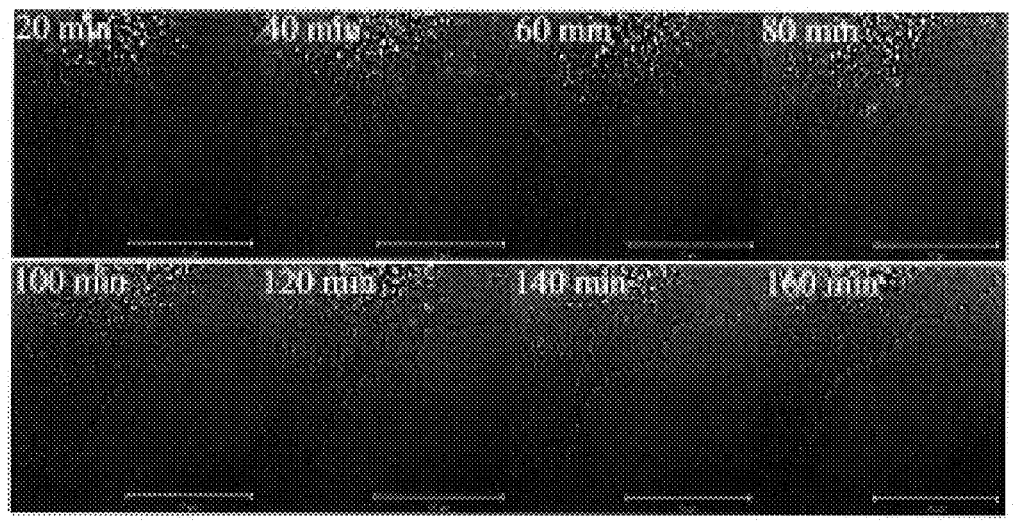

The growth dynamics of these starvation-induced protrusions and the emergence of Myo19 foci within them were further examined by performing live imaging of starved cells ectopically expressing Myo19-eGFP (FIG. 15). Most of the foci formed within the cell boundary at time zero of imaging (+20 min of starvation), which is marked by yellow line (70%. N=100 from 14 cells), whereas fewer extend beyond the cell boundary (30%. N=100 from 14 cells). However, it is impossible to conclude from these experiments what is the order of events between protrusion formation and Myo19 foci dynamics. The relation between the protrusions and Myo19 foci can also be seen in time-lapse DIC images clearly showing the linkage between them (FIG. 16A). Similar protrusions were observed in WT cells under starvation (FIG. 16B).

Thus, it is here demonstrated quantitatively a link between Myo19, its mitochondria-binding motif and glucose starvation to localization to starvation-induced foci formation in the cell periphery protrusions.

Example 8

Actin Cytoskeleton is Essential for Starvation-Induced Myo19 Foci Formation

Figure 17:
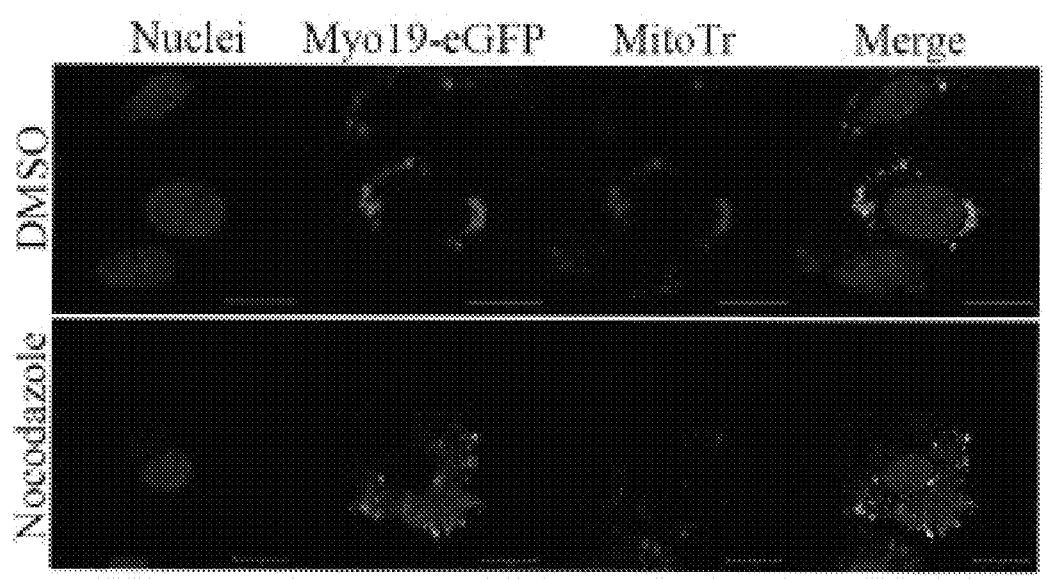
FIG. 17: Localization of myo19-eGFP under starvation conditions in cells pre-treated with the actin-depolymerizing drug Latrunculin B (LatB) or EtOH (Vehicle).

To support the results that an active motor is required for Myo19 foci formation, the effect of disruption of the actin cytoskeleton on Myo19 foci formation was tested. Treating Myo19-eGFP expressing cells with 0.2 µM latrunculin B (LatB) 30 min prior to starvation prevented the foci formation (<30% of the cells showed <2 foci), further supporting that Myo19 foci formation is via the actin cytoskeleton (FIG. 17 and FIG. 10). Alternatively, nocodazole treatment of Myo19-eGFP expressing cells induced Myo19 foci formation under complete media conditions (>80% of the cells). This is similar to the findings in cells ectopically expressing mDia1 and treated with nocodazole show strong shift towards actin based mitochondrial motility (FIG. 3C and FIG. 11).

Example 9

Starvation Induced Protrusions Possess Filopodia Markers

Figure 4C:
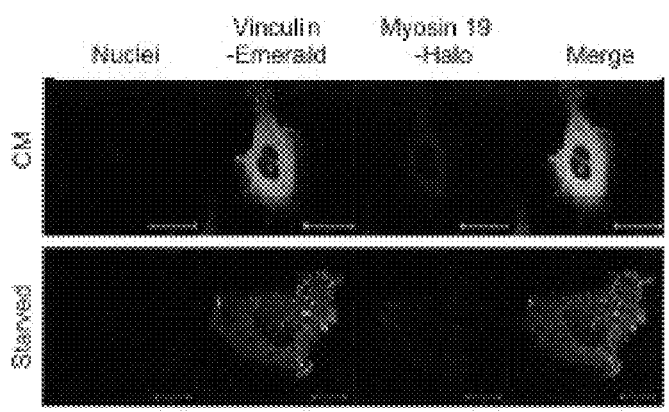
Figure 3A:
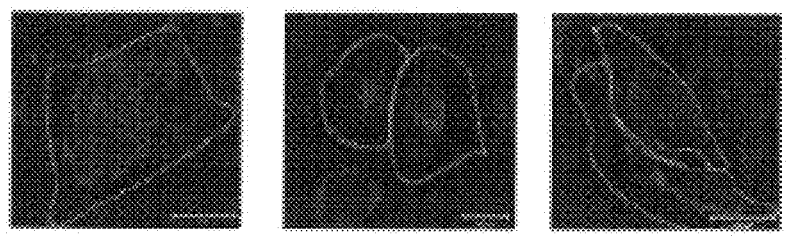
Figure 3B:
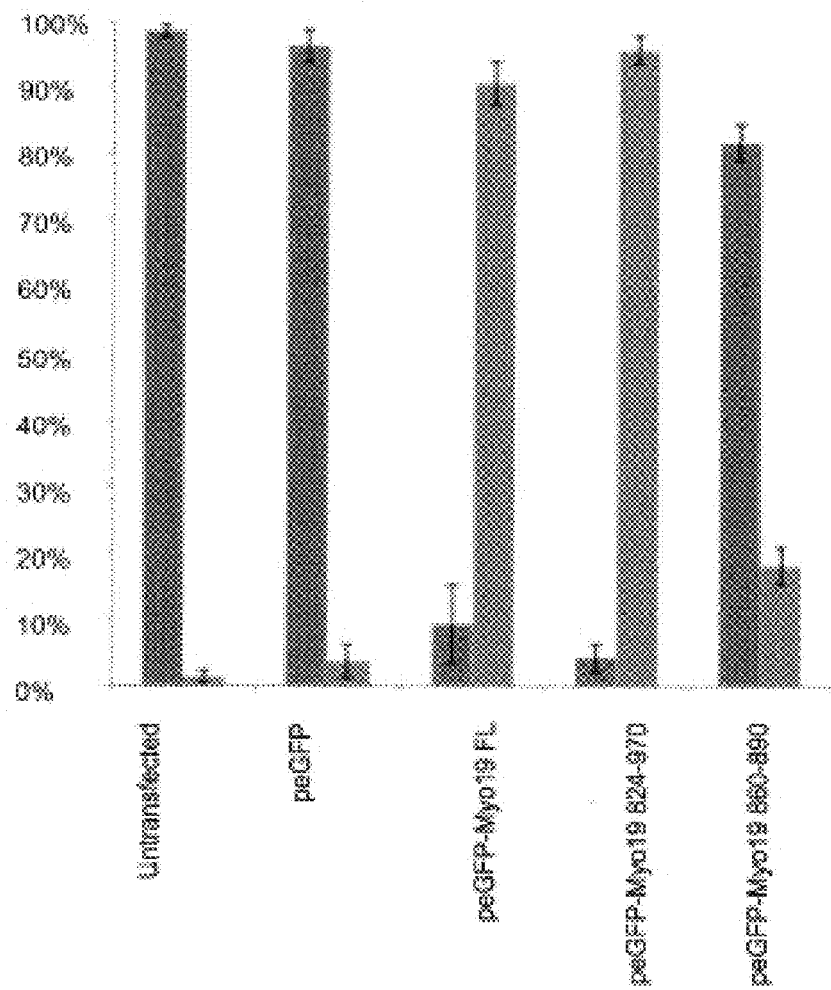

The starvation-induced localization of Halo tagged Myo19 (Myo19-Halo) with Actin-eGFP in live cells or 488-Alexa Fluor phalloidin stained actin in fixed cells was tested, revealing that Myo19 foci localized at the tips of actin protrusions (FIG. 4A FIG. 12). To characterize these actin protrusions Myo19 localization with focal adhesion and filopodia markers were tested. These structures may provide further insight regarding the nature of these protrusions. Vinculin and Paxillin were used as markers to test whether Myo19 foci are related to focal adhesions. Ectopically expressed Emerald-Vinculin localized to the base of the protrusions; however, Myo19 was localized farther towards the tip (FIG. 4C). Notably, expressing Paxillin-eGFP inhibited protrusion formation, in accordance with published literature, however it was not localized with myosin 19 in the few that formed (FIG. 4C).

Figure 18:
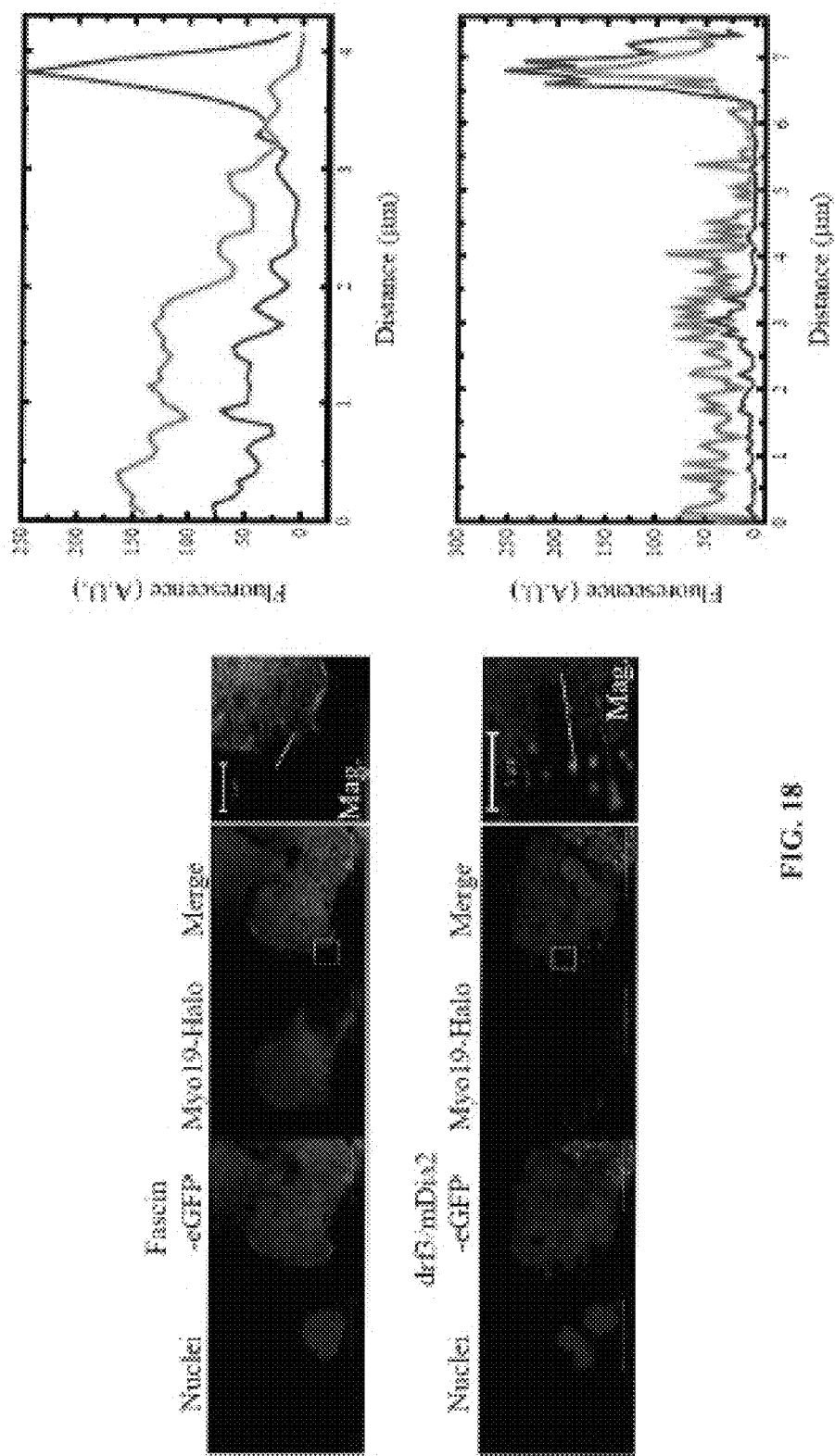
FIG. 18: Myo19-eGFP localizes to tips of filopodia in response to starvation. Ectopic expression of Myo19-Halo and Fascin-eGFP (Top) or drf3/mDia2-eGFP (Bottom) reveals that Myo19 localizes to tips of growing filopodia in response to starvation. Mag.—magnification of the white box. Intensity plot—color intensity plot of the yellow line was generated using ImageJ. Blue—nuclei, green—actin-eGFP (top) or Fascin-eGFP (bottom), red—myo19-Halo stained with TMR. Bar is 20 μm except in magnification where it is 5 μm.
Figure 19:
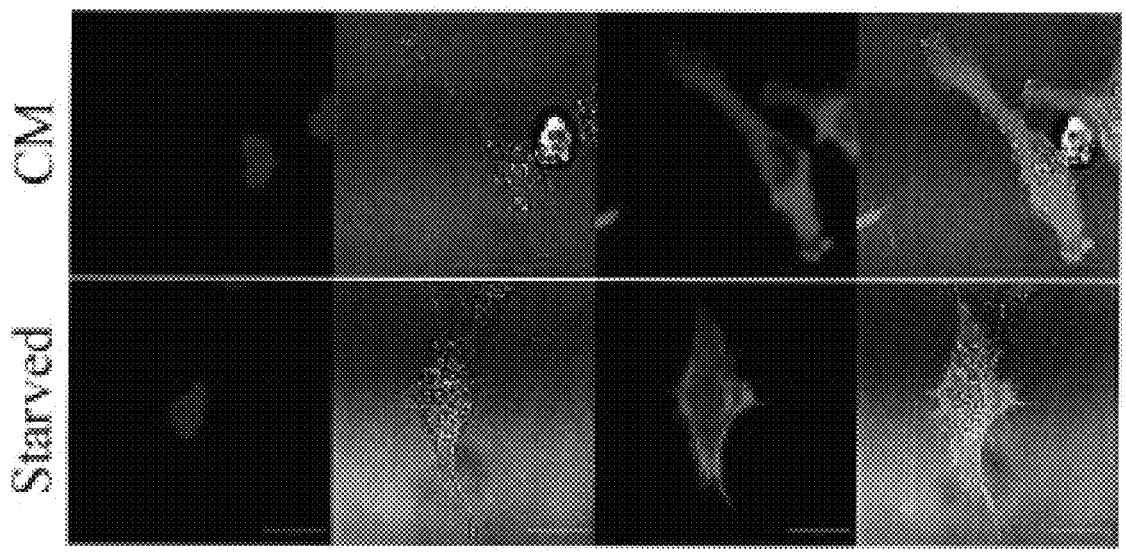
FIG. 19: Comparison of the localization of Myo19 actin, or focal adhesion markers in response to starvation or nocodazole treatment and starvation induced filopodia formation in other cell line. To test whether the starvation-induced filopodia formation was unique to the U2OS cell line we ectopically expressed Fascin-eGFP in Hela cells and starved them. Starvation-induced filopodia formation was seen in Hela cells, indicating that this is not unique feature to U2OS cell line. Bar is 20 μm.

The protrusions resembled filopodia in their structure, therefore Myo19 co-localization with the filopodia markers Fascin and drf3/mDia2 was tested, revealing that these actin protrusions are indeed growing filopodia and that Myo19 is present at their tip (FIG. 18). Glucose starvation induction of filopodia formation is not limited to U2OS cells as this was also shown in Hela cell-line (FIG. 19), suggesting that this is a universal phenotype.

Example 10

Myo19 is a De Novo Effector of Starvation-Induced Filopodia

Figure 20A:
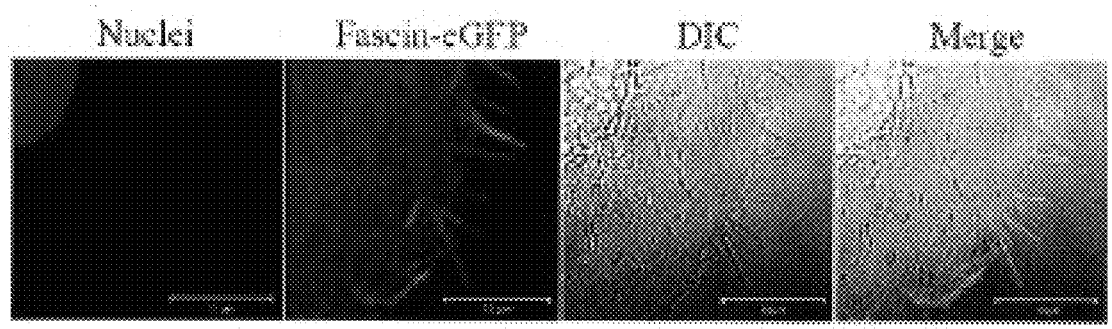
FIGS. 20A-H: Myo19 knockdown (KD) prevents filopodia formation. (20A)—Ectopic expression of fascin-eGFP and subsequent starvation verify that the protrusions seen by DIC are indeed filopodia. Blue—nuclei, green—fascin-eGFP, Bar is 10 μm. (20B)—RNAi mediated KD of endogenous Myo19 exhibits a reduced protein level expression by ~80% compared to mock RNAi treated cells. The ratio was calculated by dividing the intensity of Myo19 between the KD and the mock treatment after each has been normalized according to actin. Band intensities were measured using ImageJ. (20C)—Images showing cells expressing Fascin-eGFP under CM (Left Panel) or starvation (Right Panel) transfected with mock RNAi (upper row) or with Myo19 RNAi (lower row). The images show the strong effect on filopodia formation, length and numbers affected by Myo19
Figure 20B:
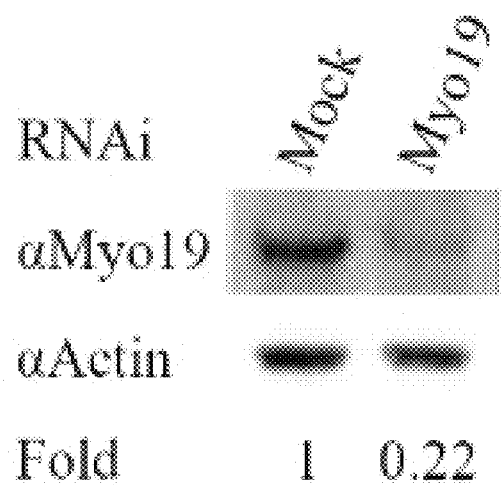
Figure 20C:
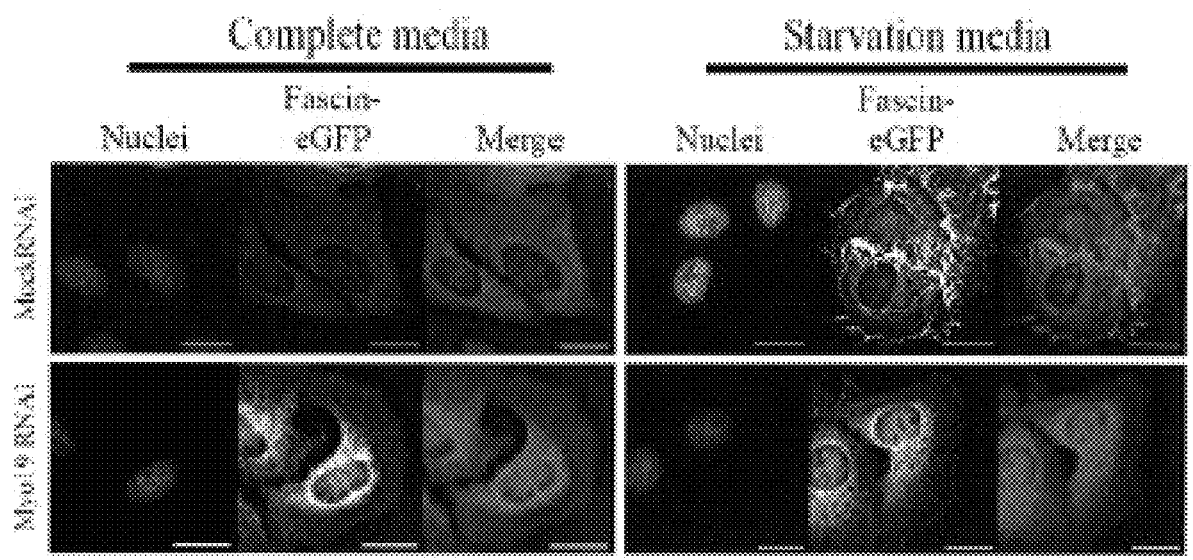
Figure 20D:
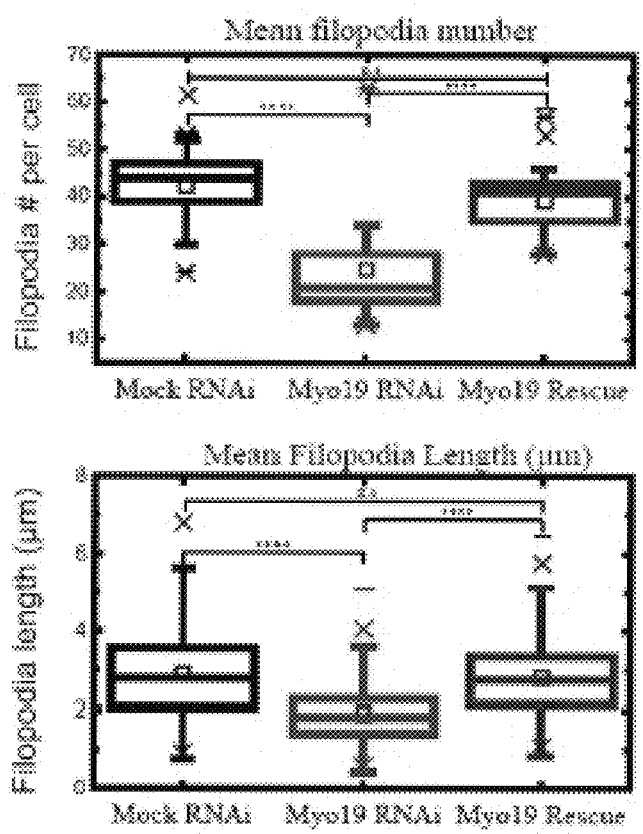
Figure 20E:
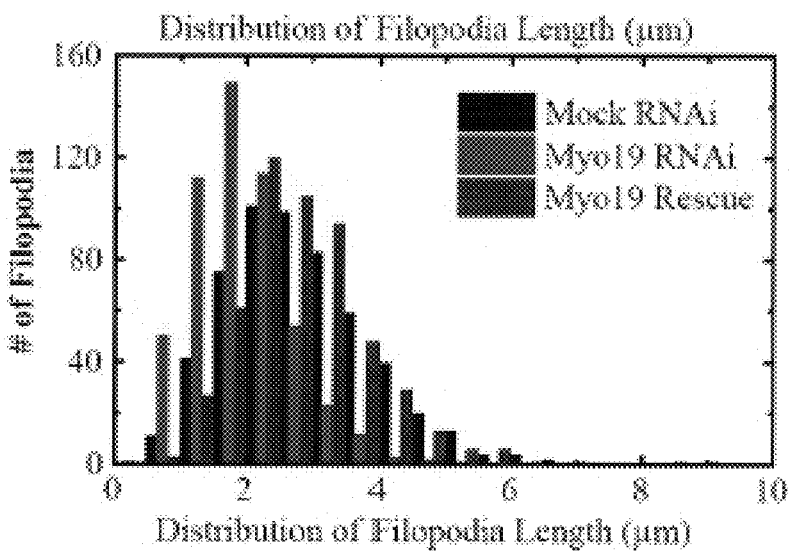
Figure 20F:
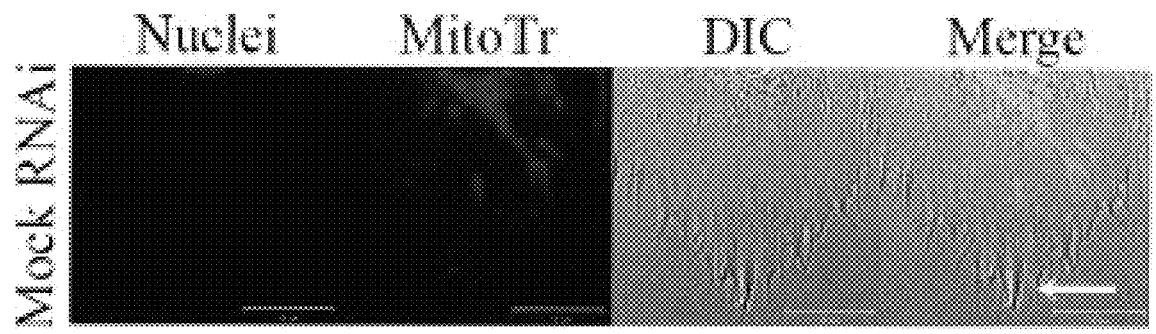
Figure 20G:
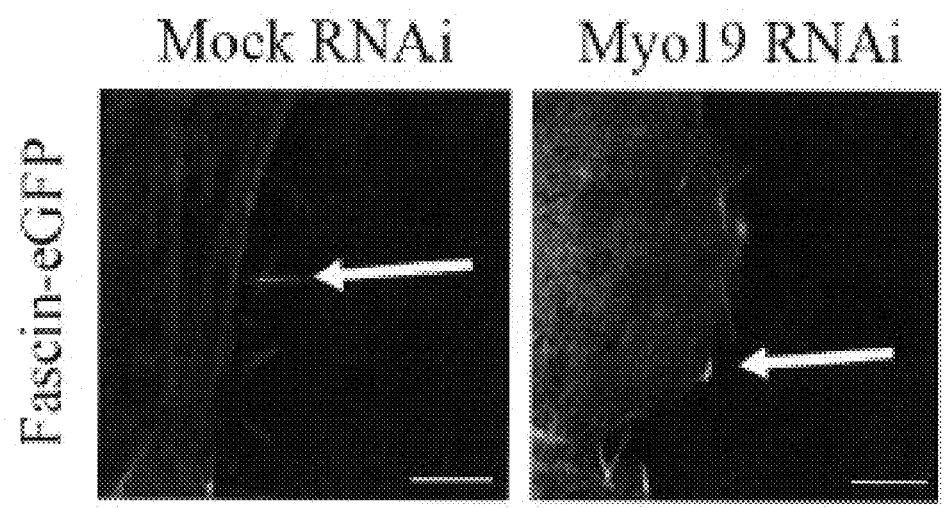
Figure 20H:
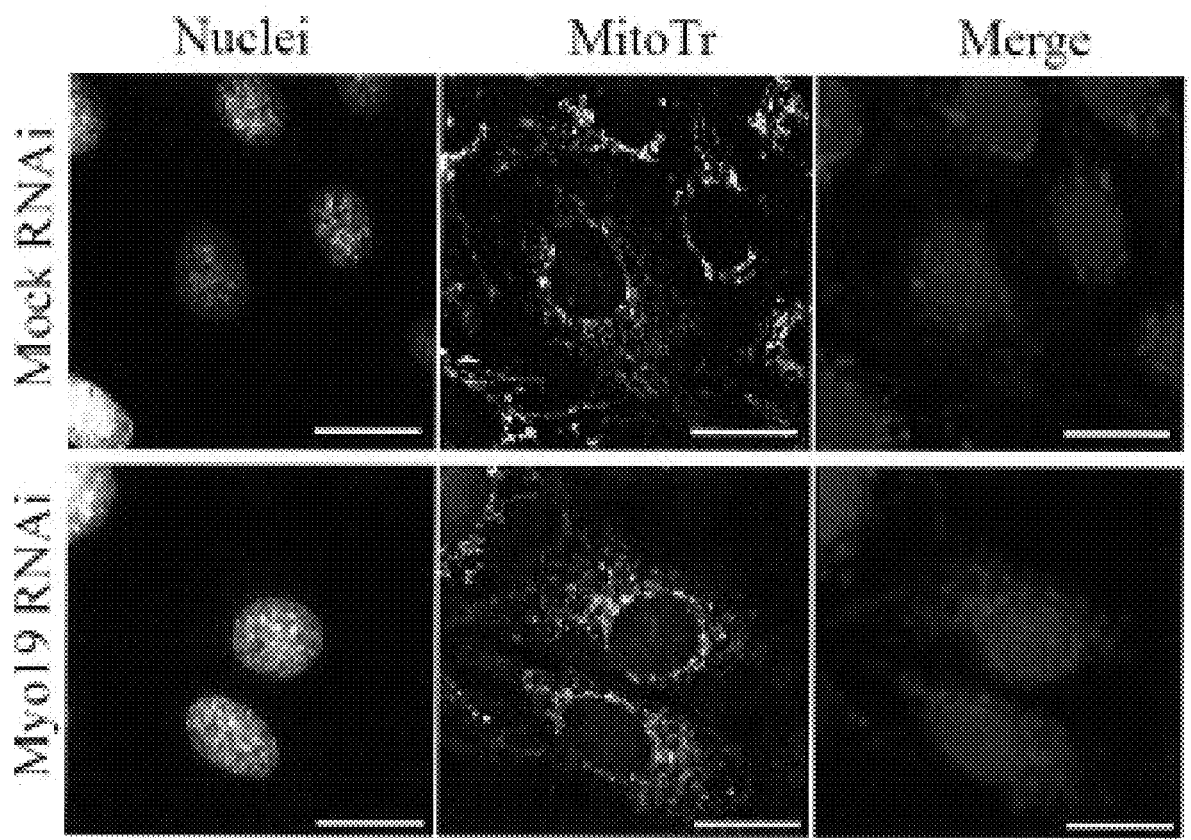

To examine Myo19 contribution to filopodia formation. RNA interference was used to knockdown (KD) Myo19 from U2OS cells and follow starvation-induced filopodia formation. Fascin-eGFP was ectopically expressed in these cells which enabled, following filopodia formation (FIG. 20A). Interestingly, filopodia formed both at the dorsal side of the cell and at the cell periphery. However, Myo19 localized only to the peripheral filopodia, but not to the dorsal filopodia, therefore only these were measured (FIG. 21A). To correctly measure their length using wide-field fluorescent microscopy, it was verified that most of the peripheral filopodia are parallel to the plane by measuring their angle at the Z-axis to be <2° (FIG. 21B). Evidentially, KD of Myo19 (~80%, FIG. 20B) resulted in significantly fewer and shorter filopodia by ~40% (from 42±7.9 to 24±10.8 filopodia per cell and from 2.9±1.22 to 1.9±0.74 µm in length, FIG. 20B and FIG. 20D). In addition, filopodia length distribution was quantified, revealing a clear shift towards shorter filopodia in Myo19 KD versus mock treated cells (FIG. 20E). The RNAi utilized to KD Myo19 was targeted against the 3' UTR, allowing us to confirm that the effects are specific to Myo19 by performing a rescue experiment, where we KD Myo19 and ectopically expressed Fascin-eGFP and Myo19-Halo. The rescue reversed the KD of Myo19 as measured by restoration of starvation-induced filopodia number to 39±6.5 filopodia per cell and length to 2.8±0.93 µm, similarly to mock treated cells (FIG. 20D). Moreover, the rescue restored filopodia length distribution to similar distribution as that of mock RNAi treated cells (FIG. 20E). Furthermore, two differences between the mock and Myo19 RNAi treated cells were observed. Mitochondria were present in a minority of the filopodia of mock treated cells, which were completely absent from filopodia of Myo19 KD cells (FIG. 20F, arrow). Additionally, Myo19 KD cells had visible patches of Fascin-eGFP at the cells periphery (FIG. 20(i)), which may represent a possible failed filopodia formation site. Comparing the rate of filopodia growth between WT cells versus Myo19 KD cells indicates that Myo19 KD cells feature a pronounced longer tag before reaching a steady state rate of filopodia growth, suggesting that Myo19 role is important for the dynamic development of filopodia (FIG. 21C). The effect of Myo19 KD on the mitochondria network morphology was tested, however no major changes were seen compared to mock treated cells (FIG. 20H). These observations strongly implicate Myo19 in starvation-induced filopodia formation.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. A composition comprising an isolated peptide of up to 40 amino acids and a molecule, said peptide comprising an amino acid sequence selected from the group consisting of:

(WVLGLVLANTAMGVGSF) ;   SEQ ID NO: 5

(IIRLWVLGLVLANTAMGVGSFQRKLVVWACL) ;   SEQ ID NO: 6
and (LLEAIIRLWVLGLVLANTAMGVGSFQRKLVVWACLQL) ,   SEQ ID NO: 7 or an analog, or a derivative thereof.

2. The composition of claim 1, wherein said isolated peptide comprises the amino acid sequence of SEQ ID NO: 5 and has a length of up to 20 amino acids.

3. The composition of claim 1, wherein said analog, or said derivative has at least 80% of the hydrophobicity characteristic of SEQ ID NO: 5.

4. The composition of claim 1, wherein said molecule is a tag selected from the group consisting of a peptide, nucleic acid, a fluorophore, a chromophore, a chemiluminescent molecule, a magnetic particle, a dye and a radioactive isotope.

5. The composition of claim 1, further comprising mitochondria.

6. A method of delivering a molecule to mitochondria of a cell, the method comprising contacting said cell with the composition of claim 1, thereby delivering said molecule to mitochondria of a cell.

7. The method of claim 6, wherein said mitochondria is the outer mitochondrial membrane (OMM).

8. A kit for assessing mitochondrial function in a cell, the kit comprising an isolated peptide of 5-40 amino acids and a molecule, said peptide comprising an amino acid sequence selected from the group consisting of:

(WVLGLVLANTAMGVGSF) ;   SEQ ID NO: 5

(IIRLWVLGLVLANTAMGVGSFQRKLVVWACL) ;   SEQ ID NO: 6
and (LLEAIIRLWVLGLVLANTAMGVGSFQRKLVVWACLQL) ,   SEQ ID NO: 7 or an analog, or a derivative thereof.

9. The kit of claim 8, further comprising at least one additional component selected from: a tag; a reagent or a buffer for isolating mitochondria; and a reagent for inducing cellular stress conditions.

* * * * *